United States Patent [19]
Pedlick et al.

[11] Patent Number: 6,041,485
[45] Date of Patent: Mar. 28, 2000

[54] SYSTEM AND METHOD FOR ANCHORING A CORD-LIKE ELEMENT TO A WORKPIECE

[76] Inventors: Jack S. Pedlick, 68 Outlook St., Butler, N.J. 07405; Felmont F. Eaves, III, 4927 Morrowick Rd., Charlotte, N.C. 28226; Vincent C. Biondo, 4 Kinney Rd., Milford, N.J. 08848

[21] Appl. No.: 09/299,837

[22] Filed: Apr. 26, 1999

Related U.S. Application Data

[62] Division of application No. 09/208,237, Dec. 9, 1998, Pat. No. 5,935,134, which is a division of application No. 08/935,215, Sep. 22, 1997, Pat. No. 5,885,294.

[51] Int. Cl.[7] .............................. B23P 11/02; A61M 5/00
[52] U.S. Cl. ................................ 29/450; 29/451; 606/72; 606/80; 606/139; 606/180; 606/232; 408/150
[58] Field of Search .......................... 29/450, 451, 235, 29/282; 408/226, 150, 1 R; 82/1.2; 407/53; 606/80, 180, 72, 213, 232, 139

[56] References Cited

U.S. PATENT DOCUMENTS

| | | |
|---|---|---|
| 2,461,947 | 2/1949 | Weber . |
| 4,531,596 | 7/1985 | Kleine ..................... 175/384 |
| 4,738,255 | 4/1988 | Goble et al. . |
| 4,815,904 | 3/1989 | Fischer ..................... 409/190 |
| 4,838,742 | 6/1989 | Fricker . |
| 4,971,486 | 11/1990 | Rinklake et al. ............ 408/180 |
| 4,989,681 | 2/1991 | Lohmuller et al. .......... 175/398 |
| 5,090,848 | 2/1992 | Haug ........................ 408/27 |
| 5,100,417 | 3/1992 | Cerier et al. . |
| 5,217,486 | 6/1993 | Rice et al. . |
| 5,236,445 | 8/1993 | Hayhurst et al. . |
| 5,258,016 | 11/1993 | DiPoto et al. . |
| 5,312,438 | 5/1994 | Johnson . |
| 5,380,334 | 1/1995 | Torrie et al. . |
| 5,417,712 | 5/1995 | Whittaker et al. ........... 606/232 |
| 5,462,393 | 10/1995 | Eischeid .................... 408/159 |
| 5,496,348 | 3/1996 | Bonutti . |
| 5,522,844 | 6/1996 | Johnson . |
| 5,540,527 | 7/1996 | Bohnet et al. .............. 408/147 |
| 5,545,180 | 8/1996 | Le et al. . |
| 5,578,057 | 11/1996 | Wenstrom, Jr. ............. 606/232 |
| 5,593,425 | 1/1997 | Bonutti et al. . |
| 5,643,320 | 7/1997 | Lower et al. . |
| 5,662,658 | 9/1997 | Wenstrom, Jr. . |
| 5,683,418 | 11/1997 | Luscombe et al. .......... 606/232 |
| 5,690,676 | 11/1997 | DiPoto et al. . |
| 5,733,307 | 3/1998 | Dinsdale .................... 606/232 |
| 5,735,650 | 4/1998 | Miyanaga ................... 408/156 |
| 5,817,095 | 10/1998 | Smith ........................ 606/79 |
| 5,885,294 | 3/1999 | Pedlick et al. .............. 606/80 |

FOREIGN PATENT DOCUMENTS

| | | |
|---|---|---|
| 0 211 997 | 3/1987 | European Pat. Off. . |
| 3022464A1 | 1/1982 | Germany .................. B28D 1/14 |
| 36 29 562 | 11/1987 | Germany . |
| 595 908 | 12/1947 | United Kingdom . |

*Primary Examiner*—David P. Bryant
*Assistant Examiner*—Essama Omgba
*Attorney, Agent, or Firm*—Alston & Bird LLP

[57] ABSTRACT

A novel system and method for anchoring a suture or other cord-like element to a bone or other workpiece. The system comprises a drill for forming an undercut hole in a bone or other workpiece, an anchor for securing a suture or other cord-like element in the undercut hole in the bone or other workpiece, and an inserter for deploying the anchor in the undercut hole in the bone or other workpiece.

7 Claims, 17 Drawing Sheets

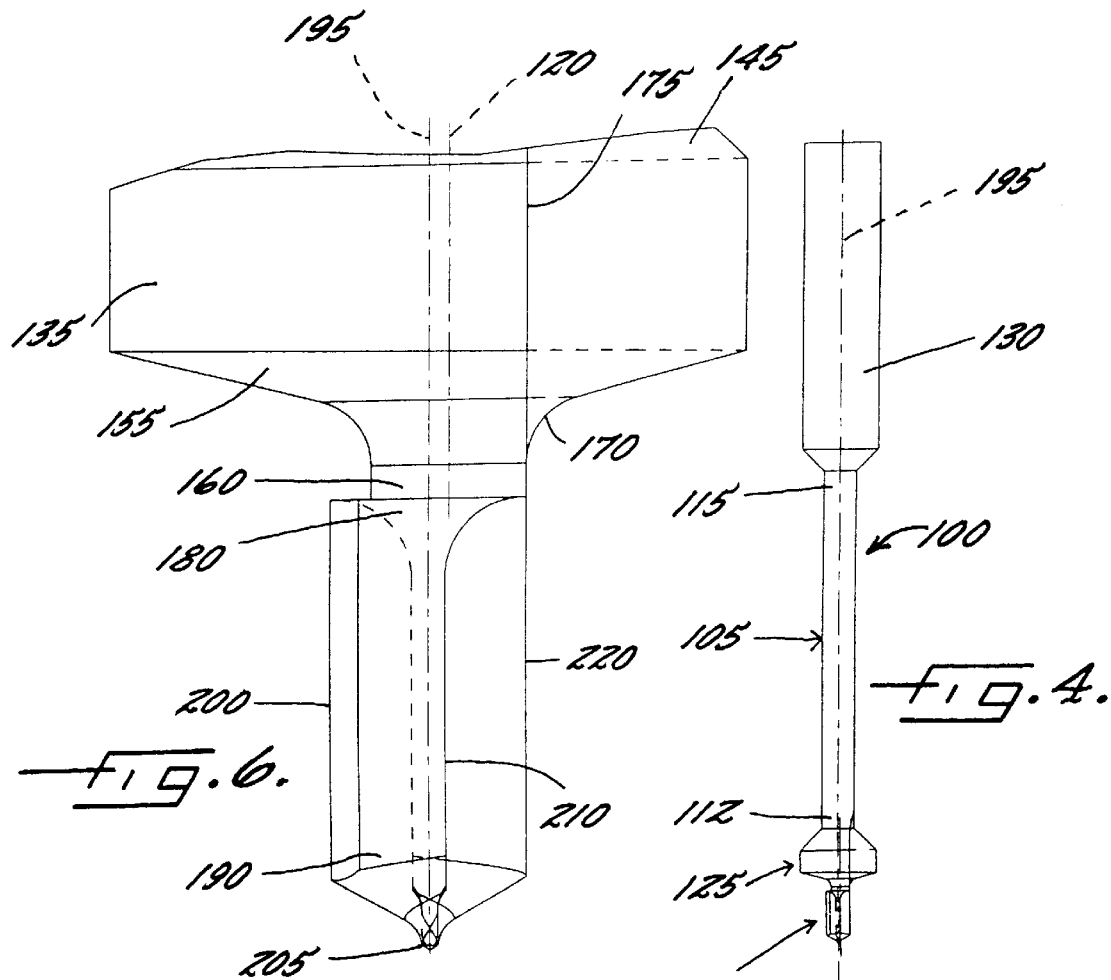
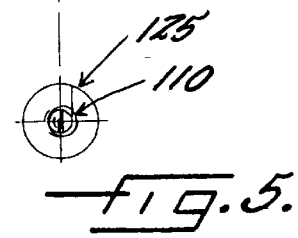
Fig. 4.
Fig. 5.
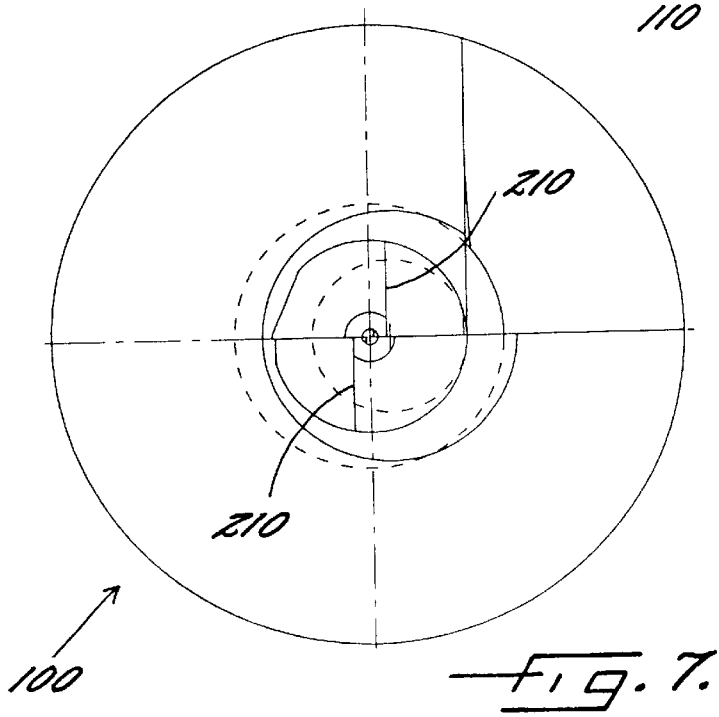
Fig. 6.
Fig. 7.

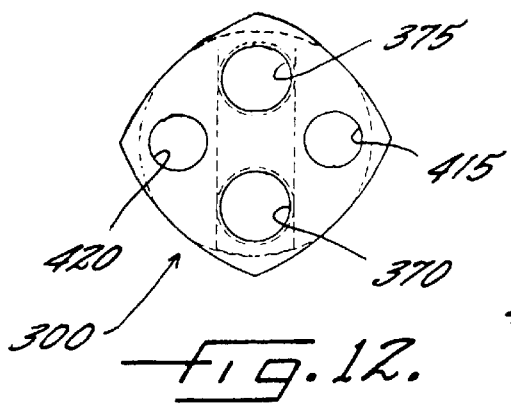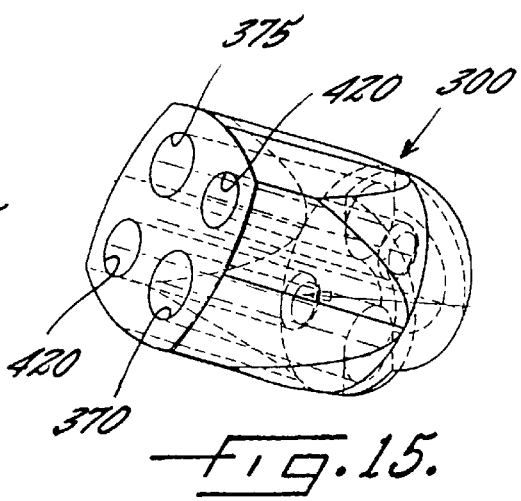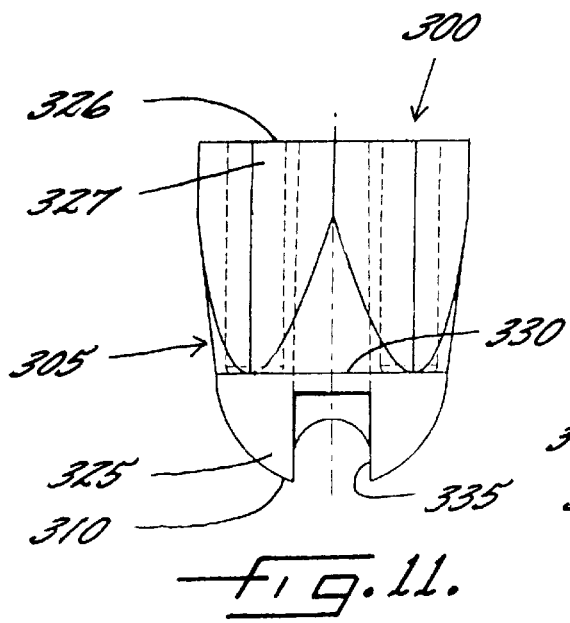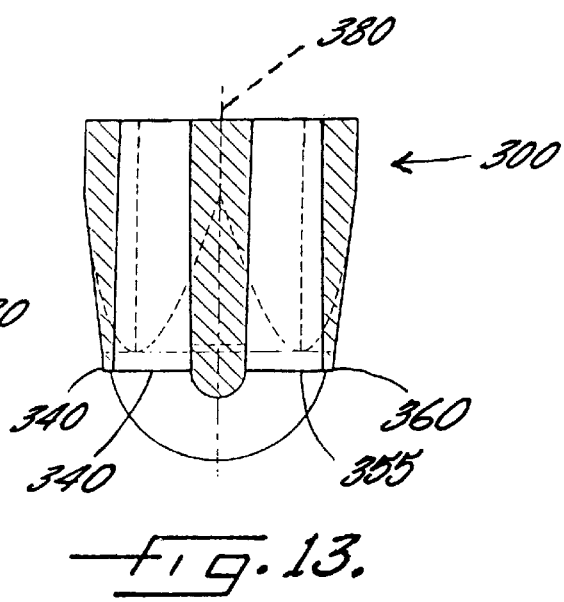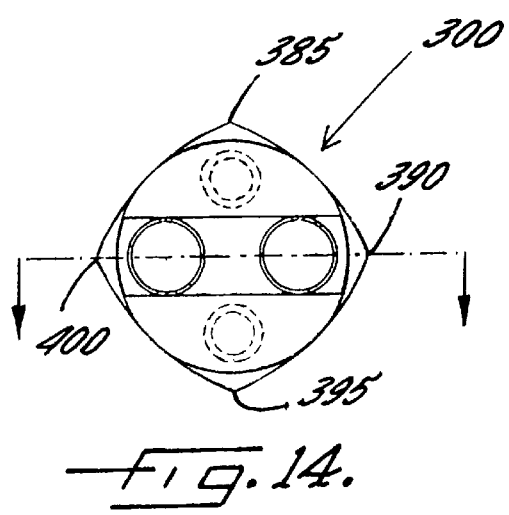

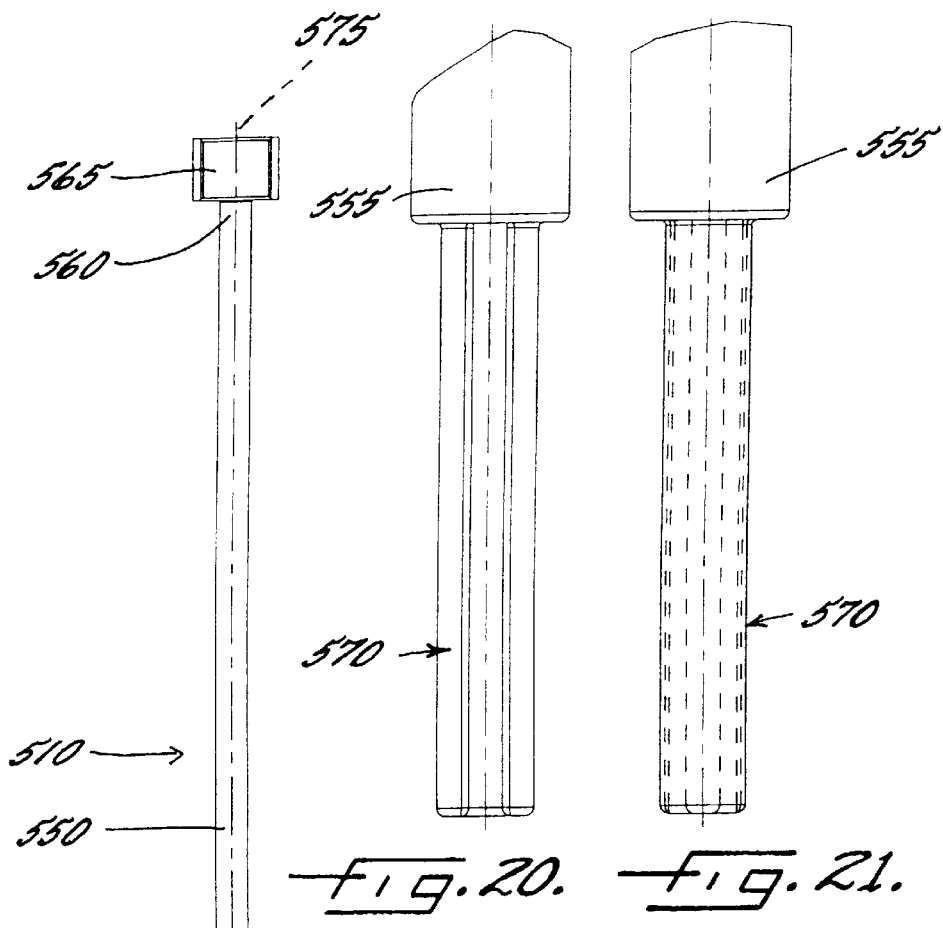
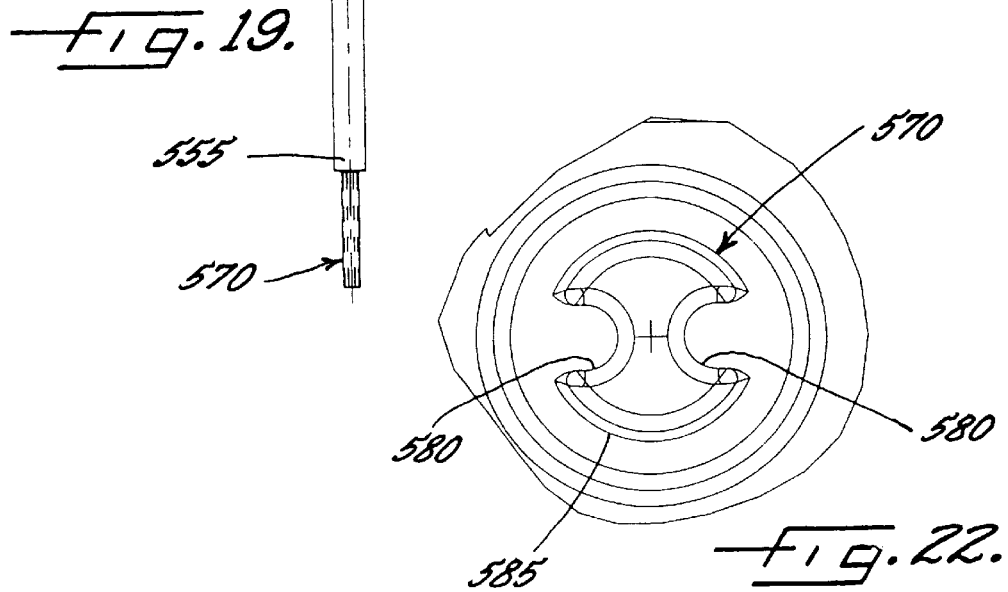

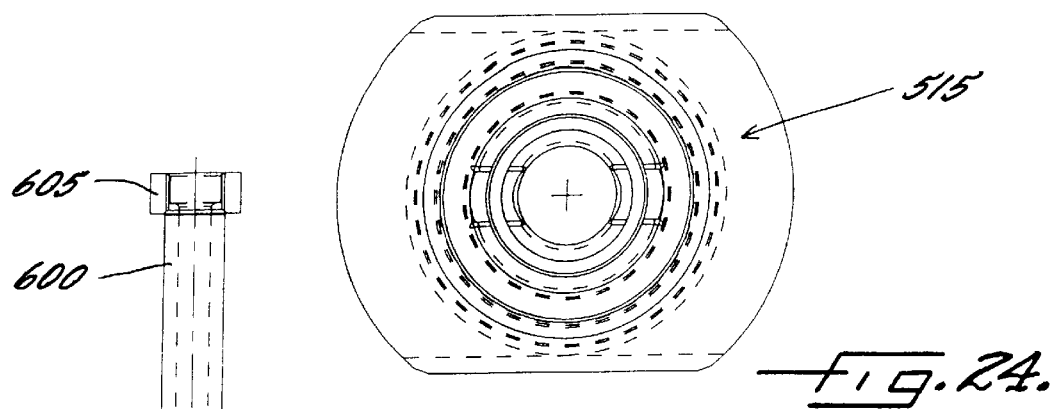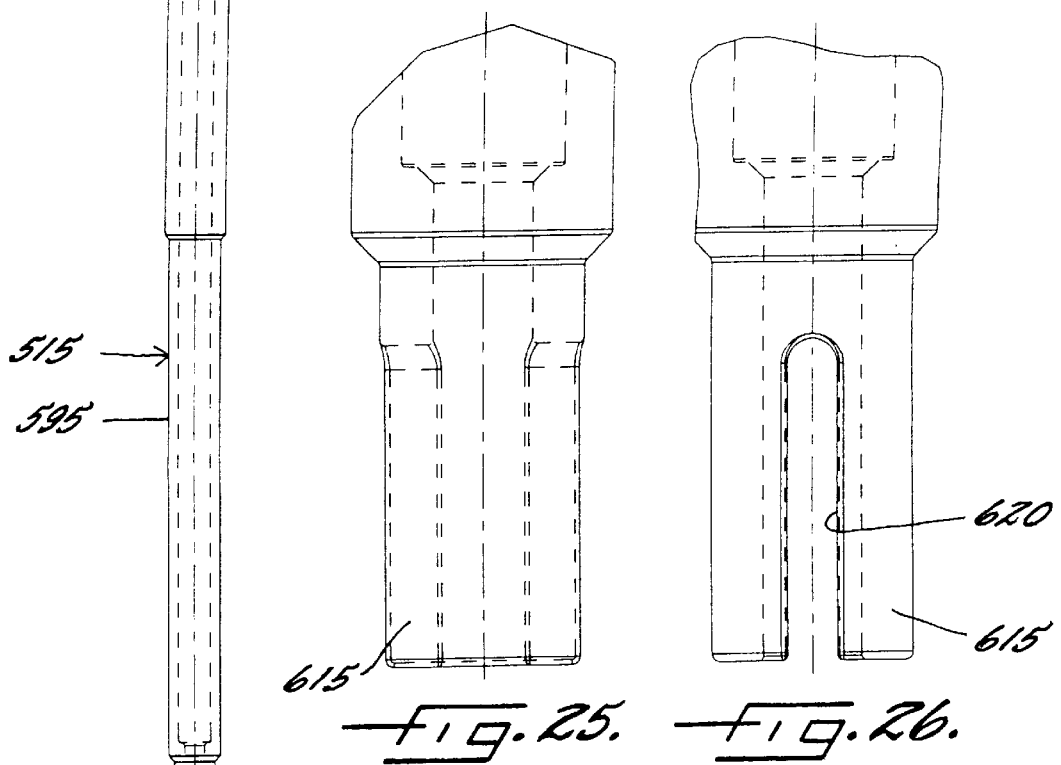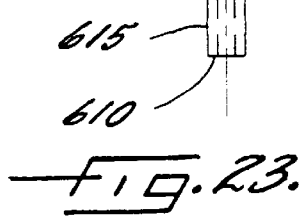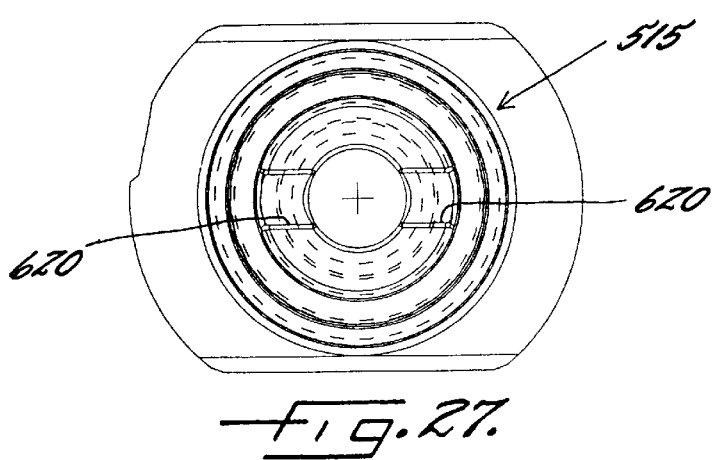

SYSTEM AND METHOD FOR ANCHORING A CORD-LIKE ELEMENT TO A WORKPIECE

RELATED APPLICATIONS

This application is a divisional of U.S. patent application Ser. No. 09/208,237 filed Dec. 9, 1998, and now U.S. Pat. No. 5,935,134, which application is a divisional of U.S. patent application Ser. No. 08/935,215 filed Sep. 22, 1997, which is now U.S. Pat. No. 5,885,294, issued Mar. 23, 1999.

FIELD OF THE INVENTION

The field of art to which this invention relates is apparatus and methods for anchoring a cord-like element to a workpiece, and more specifically suture anchors for anchoring suture material to bone.

BACKGROUND OF THE INVENTION

As the treatment of injuries to joints and soft tissue has progressed in the orthopedic medical arts, there has been a need for medical devices which can be used to attach tendons, ligaments and other soft tissue to bone. When surgically repairing an injured joint, for example, it is often preferable to restore the joint by reattaching the damaged soft tissues rather than replacing them with an artificial material. Such restorations typically require the attachment of soft tissue such as ligaments and tendons to bone.

An increase in the incidence of injuries to joints involving soft tissue has been observed. This increased incidence may be due, at least in part, to an increase in participation by the public in various physical activities such as sports and other recreational activities. These types of activities may increase the loads and stress placed upon joints, sometimes resulting in joint injuries with corresponding damage to associated soft tissue. In 1991, for example, there were approximately 560,000 surgical procedures performed in the United States in which soft tissue was attached to a bone in various joints including the shoulder, hip and knee.

One conventional orthopedic procedure for reattaching soft tissue to bone is performed by initially drilling holes or tunnels at predetermined locations through a bone in the vicinity of a joint. Then, the surgeon approximates soft tissue to the surface of the bone using sutures threaded through these holes or tunnels. This method, although effective, is a time-consuming procedure resulting in the generation of numerous bone tunnels. A known complication of drilling tunnels across bone is that nerves and other soft tissue structures may be injured by the drill bit or orthopedic pin as it exits the far side of the bone. Also, it is anatomically very difficult to reach and/or secure a suture/wire that has been passed through a tunnel. When securing the suture or wire on the far side of the bone, nerves and soft tissues can become entrapped and damaged.

In order to overcome some of the problems associated with the use of the conventional bone tunnel procedures, suture anchors have been developed and are frequently used to attach soft tissue to bone. A suture anchor is an orthopedic, medical device which is typically implanted into a cavity drilled into a bone. Although less frequently, these devices have also been referred to as bone anchors. The cavity is typically referred to as a bore hole and usually does not extend through the bone. This type of bore hole is typically referred to as a "blind hole". The bore hole is typically drilled through the outer cortex layer of the bone and into the inner cancellous layer. The suture anchor may be engaged in the bore hole by a variety of mechanisms including friction fit, barbs which are forced into the cancellous layer of bone, etc. Suture anchors are known to have many advantages including reduced bone trauma, simplified application procedures, and decreased likelihood of suture failure due to abrasion on bone. Suture anchors may be used in the Bankart shoulder reconstruction for repairing the glenohumeral ligament and may also be used in surgical procedures such as rotator cuff repair and hip replacement. Also, such anchors may be used in repair of tendon tears by direct attachment of bone to bone.

Suture anchors typically have at least one suture attached. This may be by means of a hole or opening for receiving the suture(s). At least one end and typically both ends of the suture strand extend out from the bore hole and are used to attach soft tissue. The suture anchors presently described in the art may be made of absorbable materials which absorb over time, or they may be made from various non-absorbable, biocompatible materials. Although most suture anchors described in the art are made from non-absorbable materials, the use of absorbable suture anchors may result in fewer complications since the suture anchor is absorbed and replaced by bone over time. In addition, the use of absorbable suture anchors may reduce the likelihood of damage to local joints caused by anchor migration.

Although suture anchors for attaching soft tissue to bone are available for use by the orthopedic surgeon, there is a constant need in this art for novel suture anchors having improved performance characteristics.

It has now also been recognized that suture anchors may have application in fields other than orthopedics. By way of example but not limitation, suture anchors may be employed in a field such as plastic surgery to stabilize tissue to bone. In these non-orthopedic applications, the deployment location of the suture anchor may necessitate that the suture anchor be formed as small as possible. For example, the suture anchor may need to be deployed in a relatively small facial bone. At the same time, however, the loads placed on such a suture anchor may be much less than the loads placed on an orthopedic suture anchor, thus giving rise to a range of different design considerations.

Thus there is also a need for improved suture anchors which may be used in non-orthopedic applications, including plastic surgery and the like.

SUMMARY OF THE INVENTION

These and other objects of the present invention are achieved through the provision and use of a novel system and method for anchoring a suture or other cord-like element to a bone or other workpiece.

In one form of the present invention, the system comprises a drill for forming an undercut hole in a bone or other workpiece, an anchor for securing a suture or other cord-like element in the undercut hole in the bone or other workpiece, and an inserter for deploying the anchor in the undercut hole in the bone or other workpiece.

In one form of the present invention, the drill comprises a shaft having a proximal end, a distal end and a first longitudinal axis; a re-centering element attached to the distal end of the shaft, the re-centering element including a distally-tapering portion centered on a second longitudinal axis parallel to, but laterally spaced from, a projection of the first longitudinal axis; a connecting member centered on the second longitudinal axis, the connecting member having a proximal end and a distal end, the connecting member extending distally from the re-centering member and being attached at the proximal end of the connecting member to the distally-tapering portion such that the connecting member and the distally-tapering portion together define a beveled corner centered on the second axis; and a substantially cylindrical drill head centered on an axial projection of the first longitudinal axis, the drill head having a proximal end, a distal cutting tip, an outer surface defining cutting flute means extending between the distal cutting tip and the drill head proximal end, and a transverse cross-section larger than the transverse cross-section of the connecting member; the proximal end of the drill head being eccentrically attached to the distal end of the connecting member.

In one form of the present invention, the anchor comprises a body of resilient material including a longitudinal axis, a distal end, a distal portion adjacent to the distal end, a proximal end, a proximal portion adjacent to the proximal end, and an intermediate portion connecting the distal portion to the proximal portion; the intermediate portion having a transverse cross-section sized to fit within the smallest transverse cross-section of the undercut hole in the workpiece; the proximal end defining a substantially polygonal surface sized to contain an axial projection of the transverse cross-section of the intermediate portion; the proximal portion tapering inwardly and distally from the proximal end so as to smoothly mate with the intermediate portion; the distal portion curving inwardly and distally from the intermediate portion to the distal end, and the distal end defining a curved surface which smoothly mates with the distal portion; the distal portion and the distal end together defining a substantially U-shaped groove extending from a first groove end adjacent the intermediate portion and located in alignment with one corner of the proximal end to a second groove end adjacent the intermediate portion and located in alignment with another corner of the proximal end; the groove being sized to receive a length of the cord-like material therein; a first bore extending from the first groove end to the proximal end of anchor, parallel to the longitudinal axis; a second bore extending from the second groove end to the proximal end of the anchor, parallel to the longitudinal axis; the first and second bores being sized to receive a length of the cord-like material therethrough; and a third bore extending into the proximal end of the anchor adjacent to another corner thereof, the third bore also being parallel to the longitudinal axis and extending through at least the proximal portion of the anchor.

In one form of the present invention, the inserter comprises a handle containing a biasing element; a drive rod having a rod longitudinal axis, a rod distal end, a rod proximal end, and an axial length, the proximal end of the drive rod being attached to the handle; and a sleeve having a sleeve longitudinal axis, a sleeve proximal end, a sleeve distal end, and an axial length shorter than the axial length of the drive rod; the sleeve being telescopically mounted co-axially over the drive rod and in engagement with the handle and the biasing element such that the sleeve is normally biased toward a first position wherein the sleeve distal end is located distally of the rod distal end so as to create an open cavity adapted to receive and frictionally retain at least a portion of the anchor, but may be moved proximally along the drive rod against the biasing element to a second position wherein the rod distal end projects axially and distally from the sleeve distal end.

In one form of the present invention, the method for forming an undercut bore in a workpiece comprises (a) providing a drill for forming an undercut hole in a workpiece, the drill comprising: a shaft having a proximal end, a distal end and a first longitudinal axis; a re-centering element attached to the distal end of the shaft, the re-centering element including a distally-tapering portion centered on a second longitudinal axis parallel to, but laterally spaced from, a projection of the first longitudinal axis; a connecting member centered on the second longitudinal axis, the connecting member having a proximal end and a distal end, the connecting member extending distally from the re-centering member and being attached at the proximal end of the connecting member to the distally-tapering portion such that the connecting member and the distally-tapering portion together define a beveled corner centered on the second axis; and a substantially cylindrical drill head centered on an axial projection of the first longitudinal axis, the drill head having a proximal end, a distal cutting tip, an outer surface defining cutting flute means extending between the distal cutting tip and the drill head proximal end, and a transverse cross-section larger than the transverse cross-section of the connecting member; the proximal end of the drill head being eccentrically attached to the distal end of the connecting member; (b) engaging the distal tip with the surface of the workpiece; (c) rotating the drill on the first longitudinal axis while urging the distal tip toward the workpiece so as to form a substantially cylindrical bore in the workpiece having a depth substantially equal to the axial length of the drill head plus the axial length of the connecting means; (d) further advancing the distal tip into the workpiece such that the beveled corner engages the bore, thereby shifting the axis of rotation of the drill head from the first longitudinal axis toward the second longitudinal axis and causing the drill head to enlarge the diameter of the bore below a depth substantially equal to the axial length of the connecting means; and (e) removing the drill head and the connecting means from the bore.

In one form of the present invention, the method for attaching an object to a workpiece comprises the steps of: providing a bore in the workpiece; providing a elastically compressible anchor having a longitudinal axis, a cross-section transverse to the longitudinal axis larger than the transverse cross-section of the bore adjacent the surface of the workpiece, and means for attaching an object to the anchor; axially inserting the anchor into the bore so as to secure the anchor to the workpiece; and attaching the object to the anchor.

In one form of the present invention, the method for attaching a length of cord-like material within an opening in a workpiece comprises the steps of:

(a) providing:
  a length of cord-like material;
  an anchor for securing a length of cord-like material in the undercut hole in the workpiece, the anchor comprising:
    a body of resilient material including a longitudinal axis, a distal end, a distal portion adjacent to the distal end, a proximal end, a proximal portion adjacent to the proximal end, and an intermediate portion connecting the distal portion to the proximal portion;
    the intermediate portion having a transverse cross-section sized to fit within the smallest transverse cross-section of the undercut hole in the workpiece;
    the proximal end defining a substantially polygonal surface sized to contain an axial projection of he transverse cross-section of the intermediate portion;
    the proximal portion tapering inwardly and distally from the proximal end so as to smoothly mate with the intermediate portion;

the distal portion curving inwardly and distally from the intermediate portion to the distal end, and the distal end defining a curved surface which smoothly mates with the distal portion;

the distal portion and the distal end together defining a substantially U-shaped groove extending from a first groove end adjacent the intermediate portion and located in alignment with one corner of the proximal end to a second groove end adjacent the intermediate portion and located in alignment with another corner of the proximal end;

the groove being sized to receive a length of the cord-like material therein;

a first bore extending from the first groove end to the proximal end of anchor, parallel to the longitudinal axis;

a second bore extending from the second groove end to the proximal end of the anchor, parallel to the longitudinal axis;

the first and second bores being sized to receive a length of the cord-like material therethrough; and a third bore extending into the proximal end of the anchor adjacent to another corner thereof, the third bore also being parallel to the longitudinal axis and extending through at east the proximal portion of the anchor; and an inserter for deploying a compressible anchor in the undercut hole in the workpiece, the inserter comprising:

a handle containing a biasing element;

a drive rod having a rod longitudinal axis, a rod distal end, a rod proximal end, and an axial length, the proximal end of the drive rod being attached to the handle; and a sleeve having a sleeve longitudinal axis, a sleeve proximal end, a sleeve distal end, and an axial length shorter than the axial length of the drive rod;

the sleeve being telescopically mounted co-axially over the drive rod and in engagement with the handle and the biasing element such that the sleeve is normally biased toward a first position wherein the sleeve distal end is located distally of the rod distal end so as to create an open cavity adapted to receive and frictionally retain at least a portion of the anchor, but may be moved proximally along the drive rod against the biasing element to a second position wherein the rod distal end projects axially and distally from the sleeve distal end;

(b) threading the length of cord-like material distally through the first bore in the anchor, through the groove in the anchor, and proximally through the second bore in the anchor;

(c) with the inserter in the first position, inserting the anchor proximal and first into the cavity at the distal end of the sleeve and retaining the anchor in the cavity by a frictional fit;

(d) engaging the distal end of the sleeve with the surface of the workpiece immediately surrounding the undercut opening;

(e) exerting a driving force on the handle so as to move the sleeve from its first position relative to the drive rod to its second position relative to the drive rod and to advance the distal end of the drive rod into the opening pushing the anchor ahead of it, thereby elastically deforming the anchor; and (f) removing the drive rod from the opening and the distal end of the sleeve from the surface of the workpiece.

In another form of the present invention, the method for attaching a length of cord-like material to a workpiece comprises the steps of:

(a) providing:

a length of cord-like material;

a drill for forming an undercut hole in a workpiece, the drill comprising:

a shaft having a proximal end, a distal end and a first longitudinal axis;

a re-centering element attached to the distal end of the shaft, the re-centering element including a distally-tapering portion centered on a second longitudinal axis parallel to, but laterally spaced from, a projection of the first longitudinal axis;

a connecting member centered on the second longitudinal axes, the connecting member having a proximal end and a distal end, the connecting member extending distally from the re-centering member and being attached at the proximal end of the connecting member to the distally-tapering portion such that the connecting member and the distally-tapering portion together define a beveled corner centered on the second axis; and a substantially cylindrical drill head centered on an axial projection of the first longitudinal axis, the drill head having a proximal end, a distal cutting tip, an outer surface defining cutting flute means extending between the distal cutting tip and the drill head proximal end, and a transverse cross-section larger than the transverse cross-section of the connecting member;

the proximal end of the drill head being eccentrically attached to the distal end of the connecting member;

an anchor for securing a length of cord-like material in the undercut hole in the workpiece, the anchor comprising:

a body of resilient material including a longitudinal axis, a distal end, a distal portion adjacent to the distal end, a proximal end, a proximal portion adjacent to the proximal end, and an intermediate portion connecting the distal portion to the proximal portion;

the intermediate portion having a transverse cross-section sized to fit within the smallest transverse cross-section of the undercut hole in the workpiece;

the proximal end defining a substantially polygonal surface sized to contain an axial projection of the transverse cross-section of the intermediate portion;

the proximal portion tapering inwardly and distally from the proximal end so as to smoothly mate with the intermediate portion;

the distal portion curving inwardly and distally from the intermediate portion to the distal end, and the distal end defining a curved surface which smoothly mates with the distal portion;

the distal portion and the distal end together defining a substantially U-shaped groove extending from a first groove end adjacent the intermediate portion and located in alignment with one corner of the proximal end to a second groove end adjacent the intermediate portion and located in alignment with another corner of the proximal end;

the groove being sized to receive a length of the cord-like material therein;

a first bore extending from the first groove end to the proximal end of anchor, parallel to the longitudinal axis;

a second bore extending from the second groove end to the proximal end of the anchor, parallel to the longitudinal axis;

the first and second bores being sized to receive a length of the cord-like material therethrough; and a third bore extending into the proximal end of the anchor adjacent to another corner thereof, the third bore also being parallel to the longitudinal axis and extending through at least the proximal portion of the anchor; and an inserter for deploying a compressible anchor in the undercut hole in the workpiece, the inserter comprising:

a handle containing a biasing element;

a drive rod having a rod longitudinal axis, a rod distal end, a rod proximal end, and an axial length, the proximal end of the drive rod being attached to the handle; and a sleeve having a sleeve longitudinal axis, a sleeve proximal end, a sleeve distal end, and an axial length shorter than the axial length of the drive rod;

the sleeve being telescopically mounted co-axially over the drive rod and in engagement with the handle and the biasing element such that the sleeve is normally biased toward a first position wherein the sleeve distal end is located distally of the rod distal end so as to create an open cavity adapted to receive and frictionally retain at least a portion of the anchor, but may be moved proximally along the drive rod against the biasing element to a second position wherein the rod distal end projects axially and distally from the sleeve distal end;

(b) forming an undercut hole in the workpiece with the drill by (1) engaging the distal tip of the drill head with the surface of the workpiece, (2) rotating the drill on the first axis while advancing the distal tip of the drill head into the workpiece to a depth equal to the axial length of the drill head plus the axial length of the connecting member, so as to form a substantially cylindrical bore in the workpiece, (3) advancing the distal tip further into the workpiece so as to force the beveled corner into the hole thereby causing the axis of rotation of the drill head to shift from the first longitudinal axis toward the second longitudinal axis and the drill head to radially enlarge the inner portion of the hole, and (4) removing the drill head and the connecting member from the bore through the outer, unenlarged portion of thereof;

(c) threading the length of cord-like material distally through the first bore in the anchor, through the groove in the anchor, and proximally through the second bore in the anchor;

(d) with the inserter in the first position, inserting the anchor proximal and first into the cavity at the distal end of the sleeve and retaining the anchor in the cavity by a frictional fit;

(e) engaging the distal end of the sleeve with the surface of the workpiece immediately surrounding the undercut hole;

(f) exerting a driving force on the handle so as to move the sleeve from its first position relative to the drive rod to its second position relative to the drive rod and to advance the distal end of the drive rod into the undercut hole pushing the anchor ahead of it, thereby elastically deforming the anchor as it passes through the non-enlarged portion of the undercut hole and allowing the anchor to expand to its original shape upon the completion of its entry into the enlarged portion of the undercut hole; and (g) removing the drive rod from the undercut hole and the distal end of the sleeve from the surface of the workpiece.

BRIEF DESCRIPTION OF THE DRAWINGS

These and other objects and features of the present invention will be more fully disclosed or rendered obvious by the following detailed description of the preferred embodiments of the invention, which are to be considered together with the accompanying drawings wherein like numbers refer to like parts, and further wherein:

FIGS. 4–7 are detailed views of the drill shown in FIG. 1;

FIGS. 11–15 are detailed views of the anchor shown in FIG. 2;

FIGS. 16–27 are detailed views showing various aspects of the inserter device of FIG. 3.

DETAILED DESCRIPTION OF THE PREFERRED EMBODIMENTS

Figure 1:
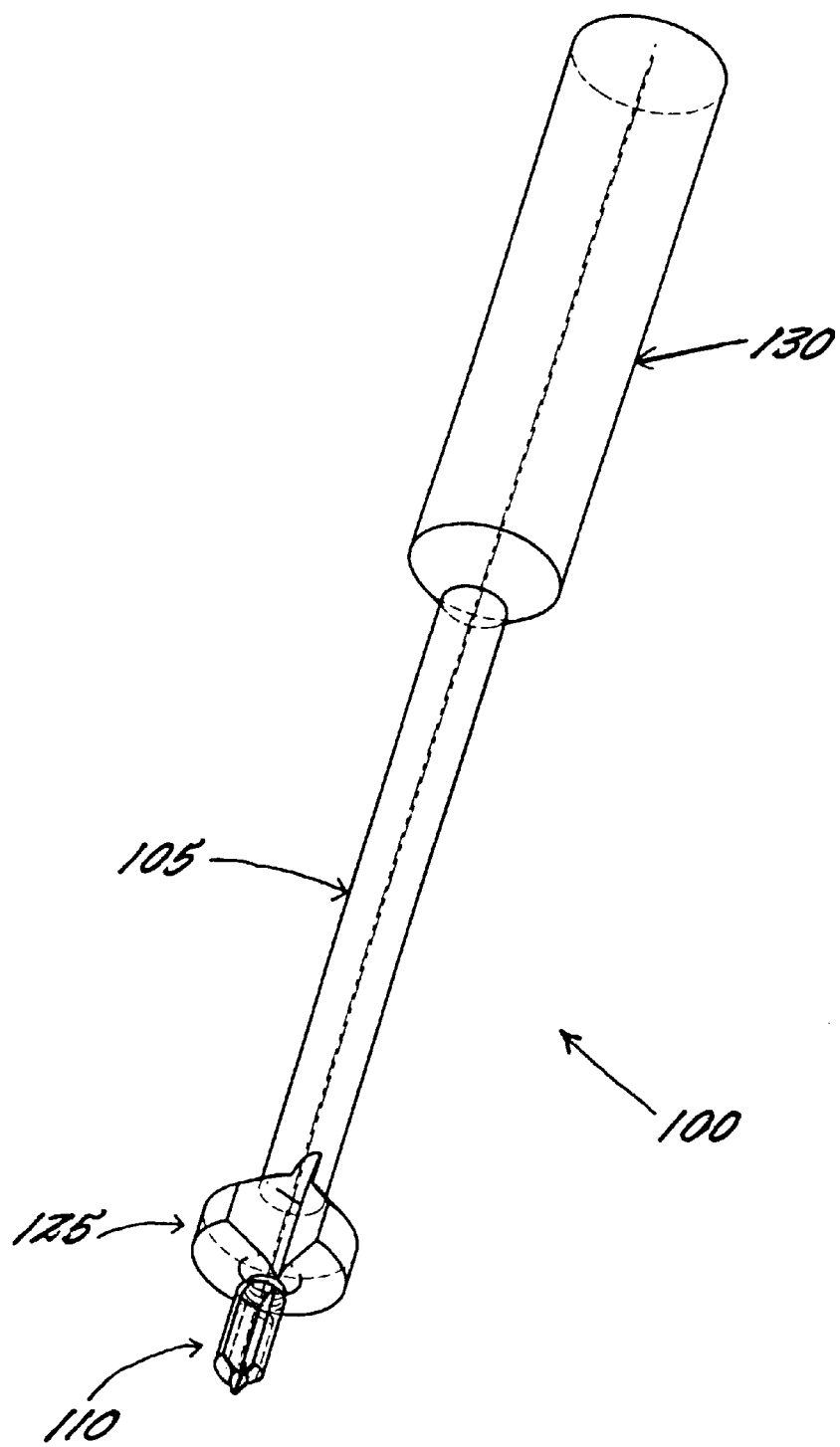
FIG. 1 is a perspective view of a drill formed in accordance with the present invention.
Figure 2:
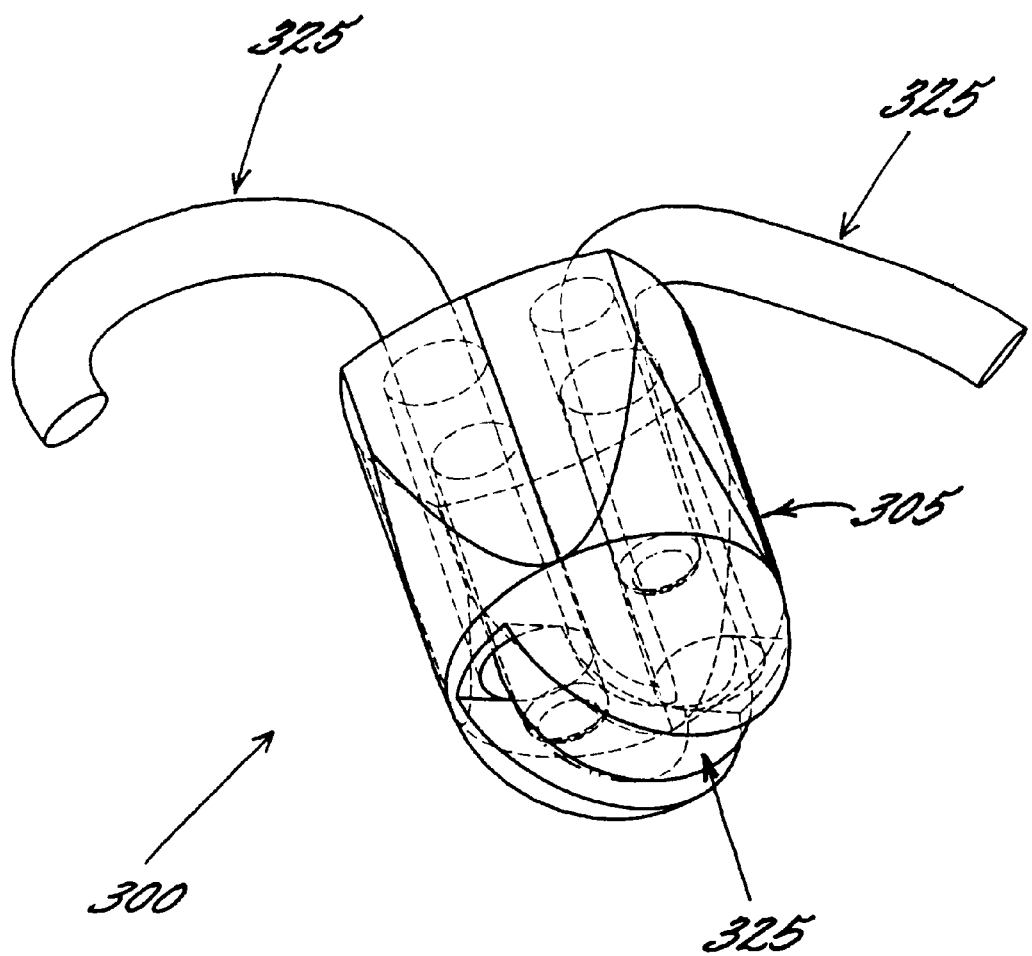
FIG. 2 is a perspective view of an anchor formed in accordance with the present invention, with a cord-like element attached thereto.

As discussed above, the present invention comprises a novel system and method for anchoring a suture or other cord-like element to a bone or other workpiece. More particularly, the novel system includes a drill 100 generally shown in FIG. 1, an anchor 300 generally show in FIG. 2, and an anchor insertion device 500 generally shown in FIG. 3. The method generally includes the steps of forming an undercut hole in the workpiece and locating an anchor (with a cord-like element attached thereto) securely within the hole, as will be discussed in detail below.

Referring specifically to FIGS. 1 and 4–7, it will be seen that drill 100 includes a shaft 105 and a drill head 110.

Shaft 105 has a shaft distal end 112, a shaft proximal end 115, a central longitudinal axis 195, and a re-centering element 125 attached to shaft distal end 112. The shaft proximal end 115 terminates in a portion 130 which is configured to be received in the chuck of a power drill or the like (not shown). Alternatively, in the event that drill 100 is to be hand driven, rather than power driver, portion 130 may be configured in the form of a handle.

Re-centering element 125 includes a central, substantially cylindrical portion 135 having a longitudinal axis aligned with shaft longitudinal axis 195, and a proximally-tapering portion 145 attached to shaft distal end 112 and having a longitudinal axis aligned with shaft longitudinal axis 195. Re-centering element 125 also comprises a distally-tapering portion 155 attached to a distally-extending connecting portion 160. Distally-tapering portion 155 and distally-extending connecting portion 160 are centered about a longitudinal axis 120. Longitudinal axis 120 is laterally offset from longitudinal axis 195 in the manner shown in FIG. 6. The angle of taper of proximally-tapering portion 145 relative to longitudinal axis 195 is substantially smaller than the angle of taper of distally-tapering portion 155 relative to longitudinal axis 120. Distally-tapering portion 155 and connecting portion 160 together define a beveled corner 170 at their intersection. Beveled corner 170 is also centered about longitudinal axis 120, which longitudinal axis is laterally offset from the above-mentioned longitudinal axis 195. Preferably beveled corner 170 comprises a radius. Re-centering element 125 also preferably defines a cutting flute 175 which extends from shaft distal end 112 to connecting portion 160, i.e., through proximally-tapering portion 145, cylindrical portion 135, distally-tapering portion 155 and beveled corner 170.

Drill head 110 is connected to the distal end of connecting portion 160. Drill head 110 has a drill head proximal end 180 and a drill head distal end 190. Drill head 110 is centered about the aforementioned longitudinal axis 195. Drill head 110 also includes an outer surface 200 defining a distal cutting tip 205 at drill head distal end 190, and at least one, and preferably a pair, of cutting flutes 210 extending from cutting tip 205 to drill head proximal end 180.

The diameter of connecting portion 160 is selected to be smaller than the diameter of drill head 110, such that when drill head 110 is attached to connecting portion 160, an edge 220 of drill head 110, located between an adjacent pair of cutting flutes 210, is located on an axial projection of the aforementioned cutting flute 175.

Figure 8:
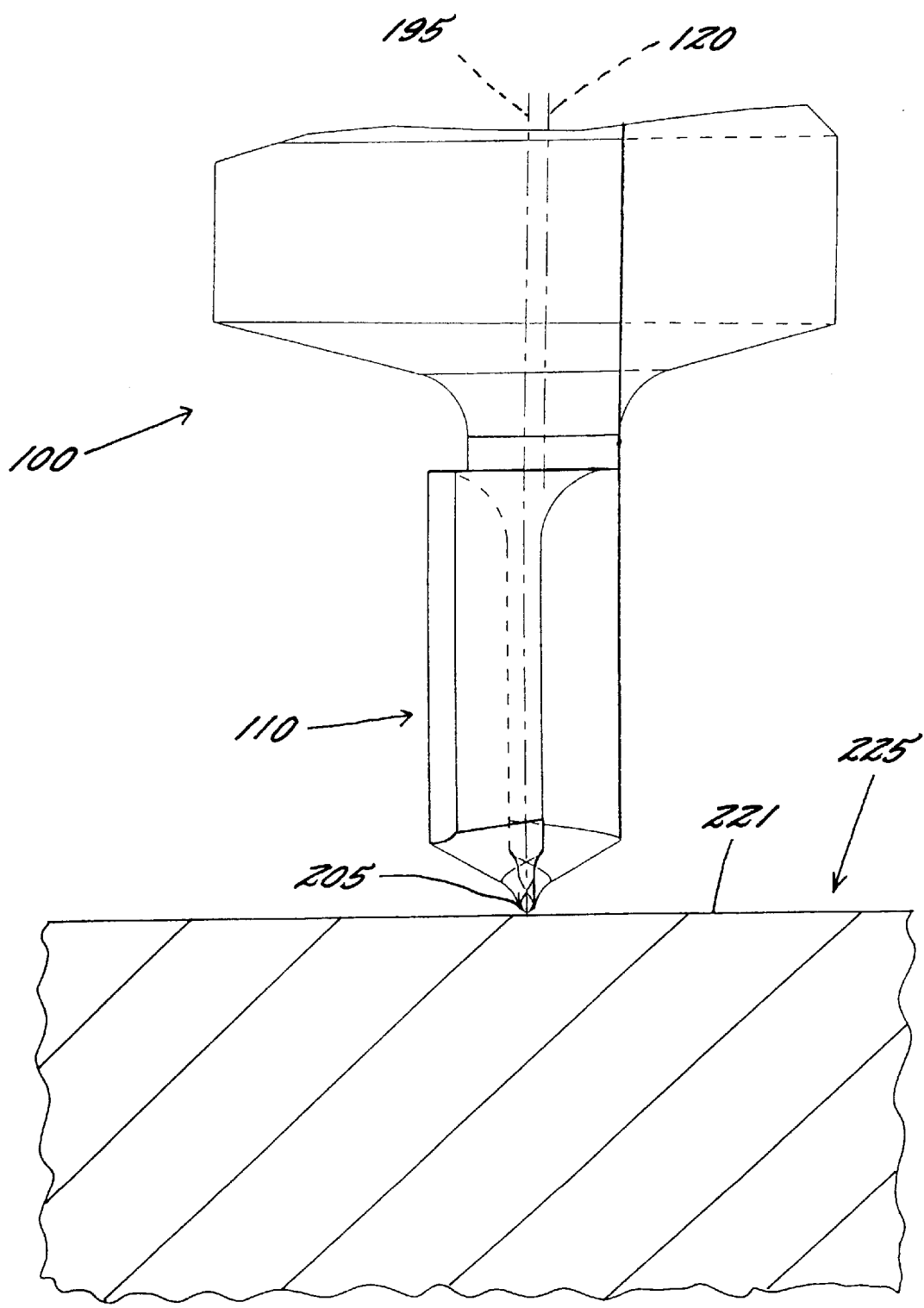
FIGS. 8–10 show the drill of FIG. 1 forming an undercut hole in a workpiece.
Figure 9:
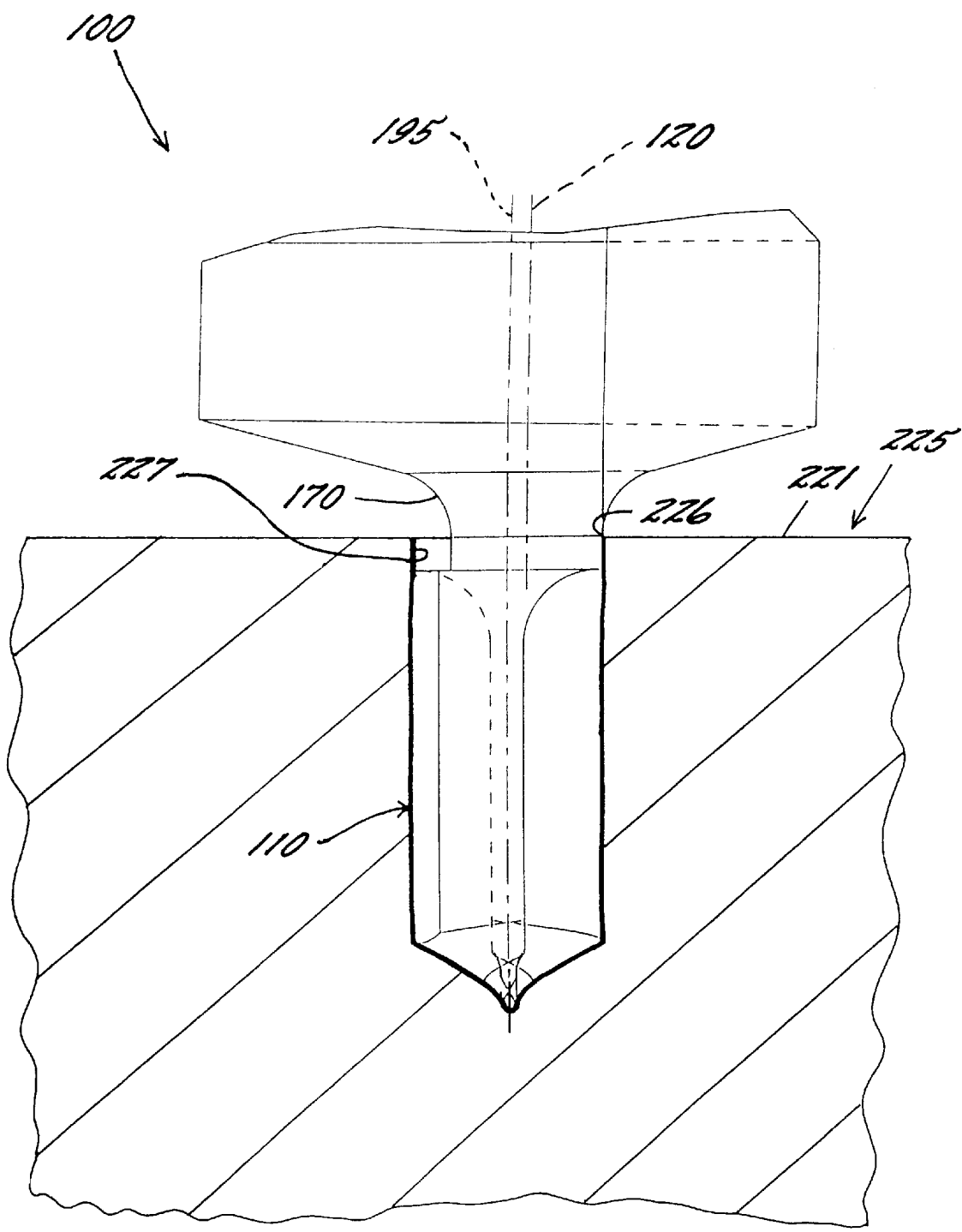
Figure 10:
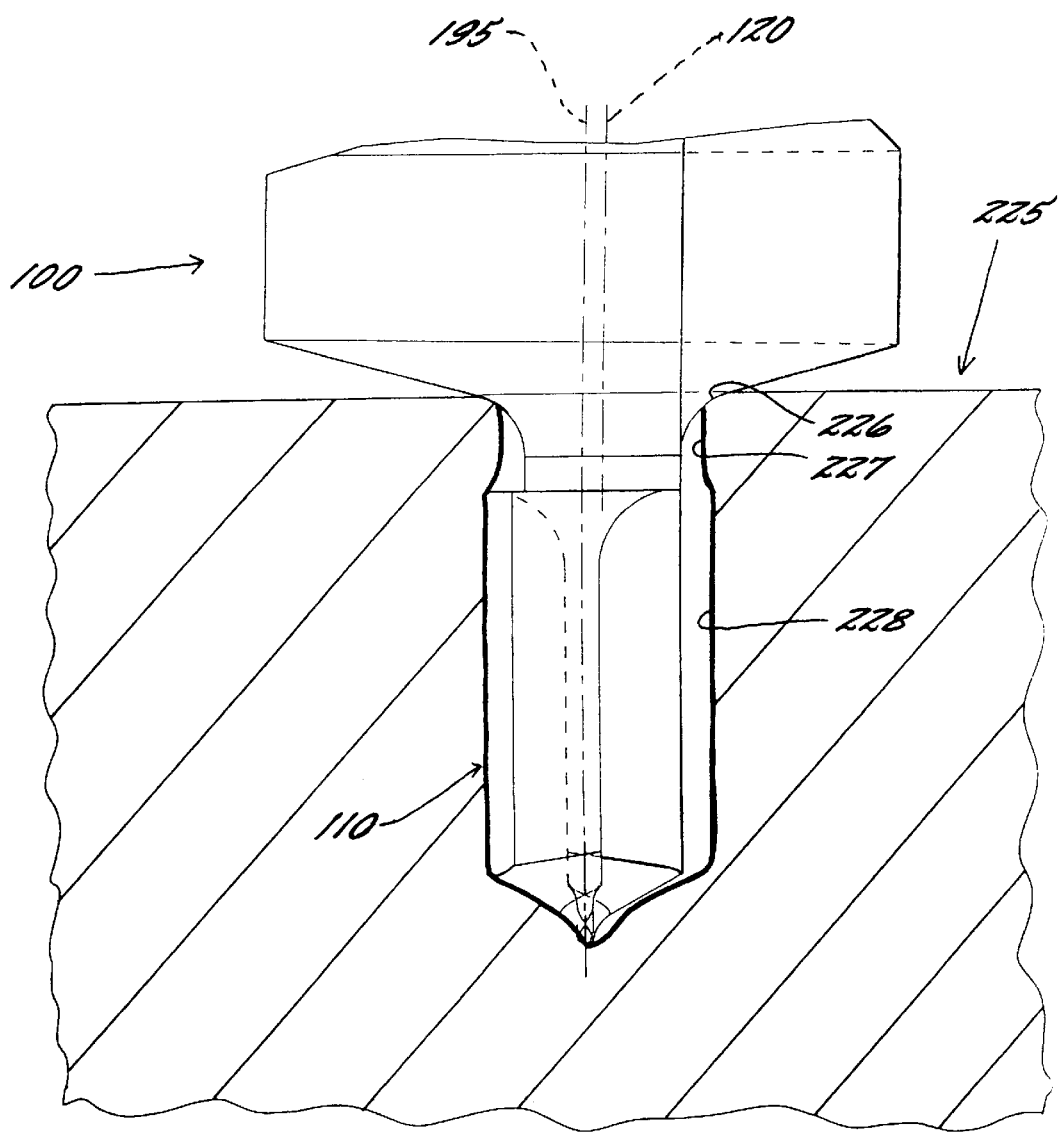

As will hereinafter be described in greater detail, the foregoing drill 100 may be conveniently used to form an undercut hole in a piece of bone or other workpiece. More specifically, the distal cutting tip 205 may be placed against a surface 221 of the workpiece 225 (FIG. 8), and the drill head 100 may be rotated on its longitudinal axis 195. This will cause drill head 110 to form an initial bore 227 in the workpiece (FIG. 9). When this bore 227 reaches a depth equal to the axial length of drill head 110 plus the axial length of connecting portion 160, however, the beveled corner 170 will engage the edge 226 of the bore 227 at the surface 221 of the workpiece. In this respect it is to be appreciated that the longitudinal axis 120 of the beveled corner 170 is laterally offset from the shaft's longitudinal axis 195. Accordingly, as the drill head continues to advance into the workpiece, the axis of rotation of drill head 110 will shift laterally from the shaft's longitudinal axis 195 to the beveled corner's longitudinal axis 120. The effect will be to gradually force the movement of drill head 110 laterally so as to undercut the workpiece and form a second bore 228 at a depth substantially equal to the axial length of connecting portion 160 plus beveled corner 170 (FIG. 10). It should also be appreciated that as this occurs, cutting flute 175 of the re-centering element 125 will form a countersunk portion at the opening of bore 227.

Referring next to FIGS. 2 and 11–15, it will be seen that the anchor 300 comprises a block of material having natural resiliency. This block comprises a body 305 which includes a distal end 310, a distal portion 325 adjacent to the distal end 310, a proximal end 326, a proximal portion 327 adjacent to the proximal end 326, and an intermediate portion 330 connecting distal portion 325 to proximal portion 327.

More particularly, intermediate portion 330 has a substantially cylindrical cross-section having a diameter slightly smaller than the diameter of drill head 110. The distal portion 325 curves inwardly from intermediate portion 330 to curved distal end 310. Further, distal end 310 and distal portion 325 together define a groove 335 (FIG. 11) which extends from a first end 340 (FIG. 13) (adjacent one side 345 of intermediate portion 330), across distal end 310 to a second end 355 (adjacent another side 360 of intermediate portion 330). Groove 335 is adapted to receive a suture or other cord-like element 365 (FIG. 2) bent in a substantially U-shaped configuration.

Bores 370, 375 (FIG. 12) extend from groove ends 340 and 355, respectively, to proximal end 326, parallel to the longitudinal axis 380 (FIG. 13) of body 305. Bores 370 and 375 each have a cross-sectional size and shape adapted to accommodate the suture or other cord-like element 365. Hence, the suture or other cord-like element 365 may be threaded through bore 370, across groove 335 and back through bore 375 (see FIG. 2). Preferably bores 370 and 375, and the suture or other cord-like element 365, are sized so that the suture or other cord-like element does not completely fill, in a diametrical sense, bores 370 and 375.

The proximal end 326 of the anchor is substantially rectangular in shape, such that an axial projection of the circular cross-section of intermediate portion 330 will fit within the boundaries of rectangular proximal end 326. Accordingly, it will be understood that proximal portion 327 of body 305 tapers inwardly from corners 385, 390, 395 and 400 (FIG. 14) of proximal end 326, respectively, so as to smoothly mate with intermediate portion 330. In view of this construction, suture anchor 300 essentially has four projections or lobes projecting radially beyond the circumference of the anchor's intermediate portion 330. Preferably the walls extending between corners 385, 390, 395 and 400 are curved slightly so as to form curved lobes projecting radially beyond the anchor's intermediate portion 330. In one preferred form of the invention, each of the walls extending between the corners 385, 390, 395 and 400 comprise a radius.

The openings of bores 370 and 375 onto proximal end 326 are located adjacent to opposite corners 390 and 400, respectively. Further, bores 415 and 420 extend into proximal end 326 adjacent to opposite corners 385 and 395, respectively. Bores 415 and 420 need not necessarily extend all the way through body 305. Thus, as shown in the drawings, bores 415 and 420 extend from the proximal end 326 of body 305 parallel to one another, and parallel to the anchor's longitudinal axis 380, to closed ends located in intermediate portion 330 of body 305.

Since the suture or other cord-like element 365, extending through bores 370 and 375, does not completely fill bores 370 and 375, and since the suture or other cord-like element 365 is generally formed of a woven material which may be compressed, it will be seen that the natural plasticity of the anchor material, together with longitudinal bores 370, 375, 415 and 420, allow the proximal, generally rectangular cross-section of the body to be substantially elastically compressed. Accordingly, anchor body 305 may be easily compressibly deformed so as to fit through the outer portion 227 of the undercut hole formed by the drill 100 in workpiece 225, and thereafter allowed to elastically expand to its normal shape within the undercut portion 228 of the hole so as to securely anchor the suture or other cord-like element 365 to the workpiece. By placing one of the holes 370, 375, 415 and 420 next to each of the corners 385, 390, 395 and 400, space is provided within the body of the anchor for the corners to deflect radially inwardly during anchor insertion. This helps prevent the anchor from deforming longitudinally during anchor insertion.

By way of example but not limitation, anchor 300 may be formed out of a non-absorbable polymer such as polysulfone or an absorbable polymer such as polylactic acid (PLA).

A specialized inserter device 500 has been found to be particularly useful in the emplacement of an anchor as just described into an undercut hole in a workpiece. This inserter device 500 is generally shown in FIG. 3, and more particularly illustrated in FIGS. 16–27.

Figure 3:
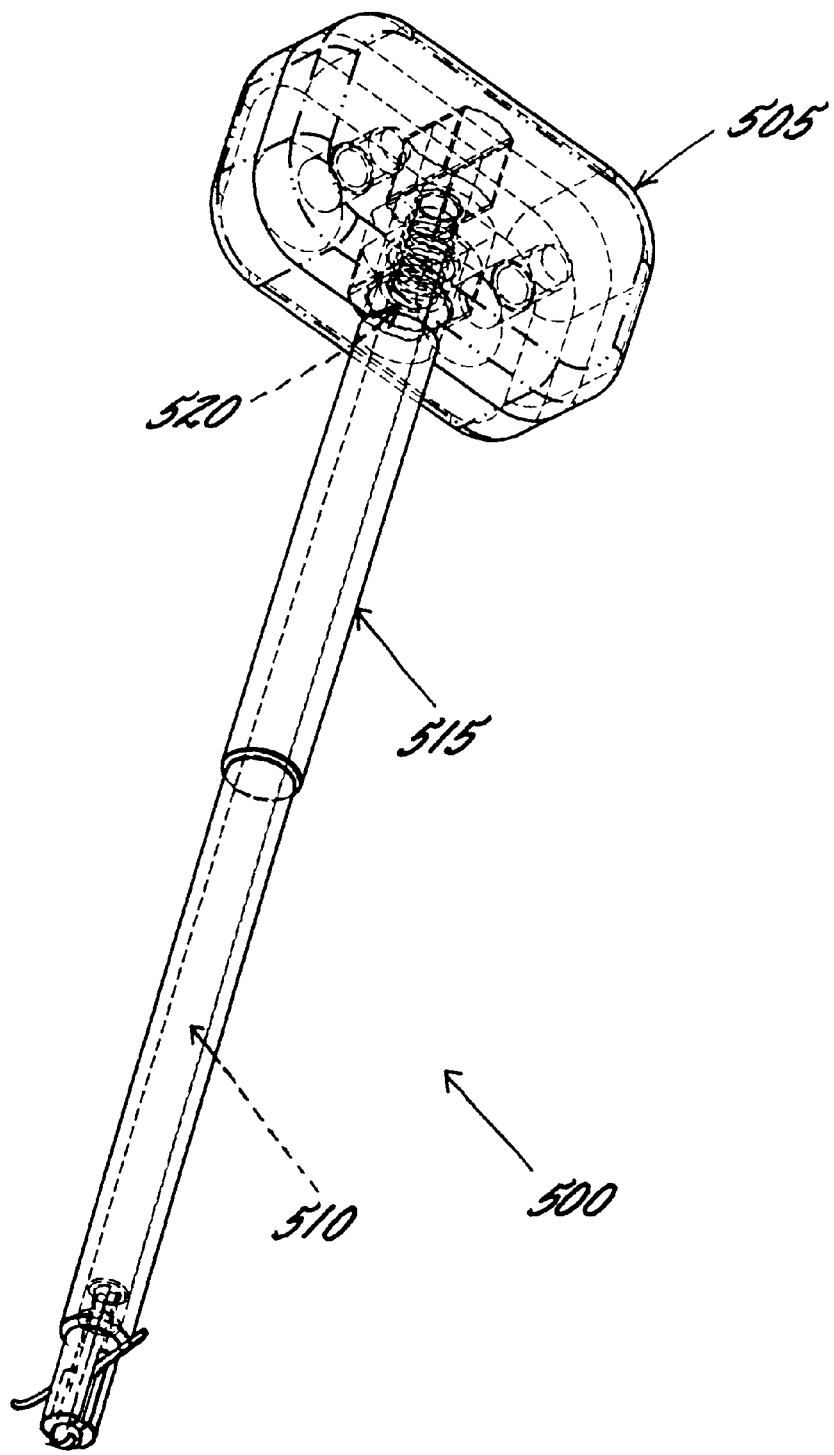
FIG. 3 is a perspective view of an inserter device for deploying the anchor shown in FIG. 2.

Inserter device 500 includes a handle 505 (FIGS. 3 and 16–18), a drive rod 510 (FIGS. 3 and 19–22), a sleeve 515 (FIGS. 3 and 23–27), and biasing means 520 (FIG. 3).

Figures 16, 18:
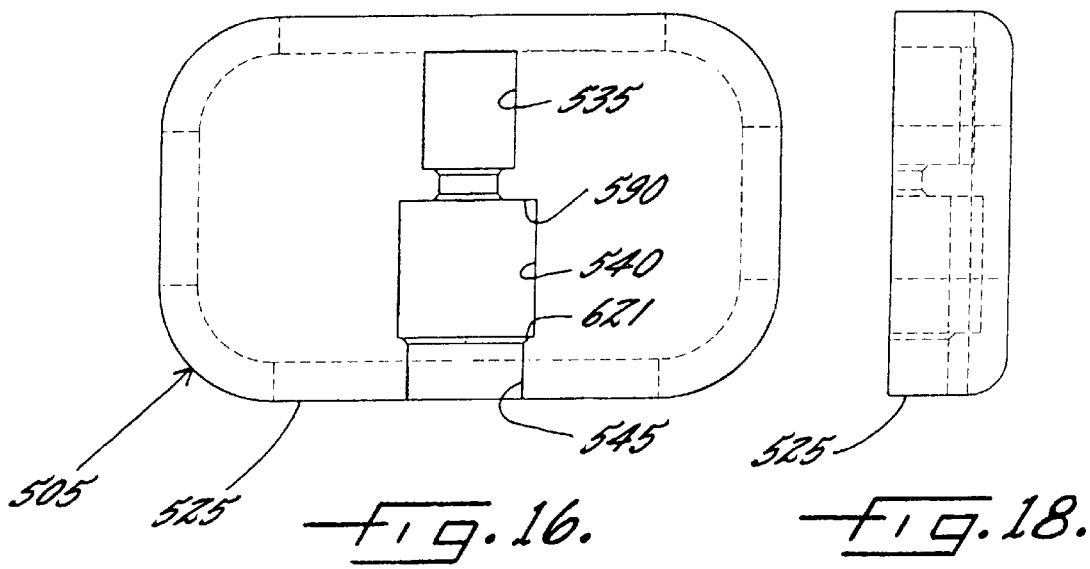
Figure 17:
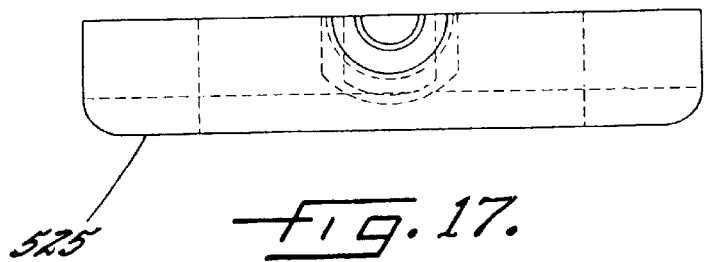
Figure 28:
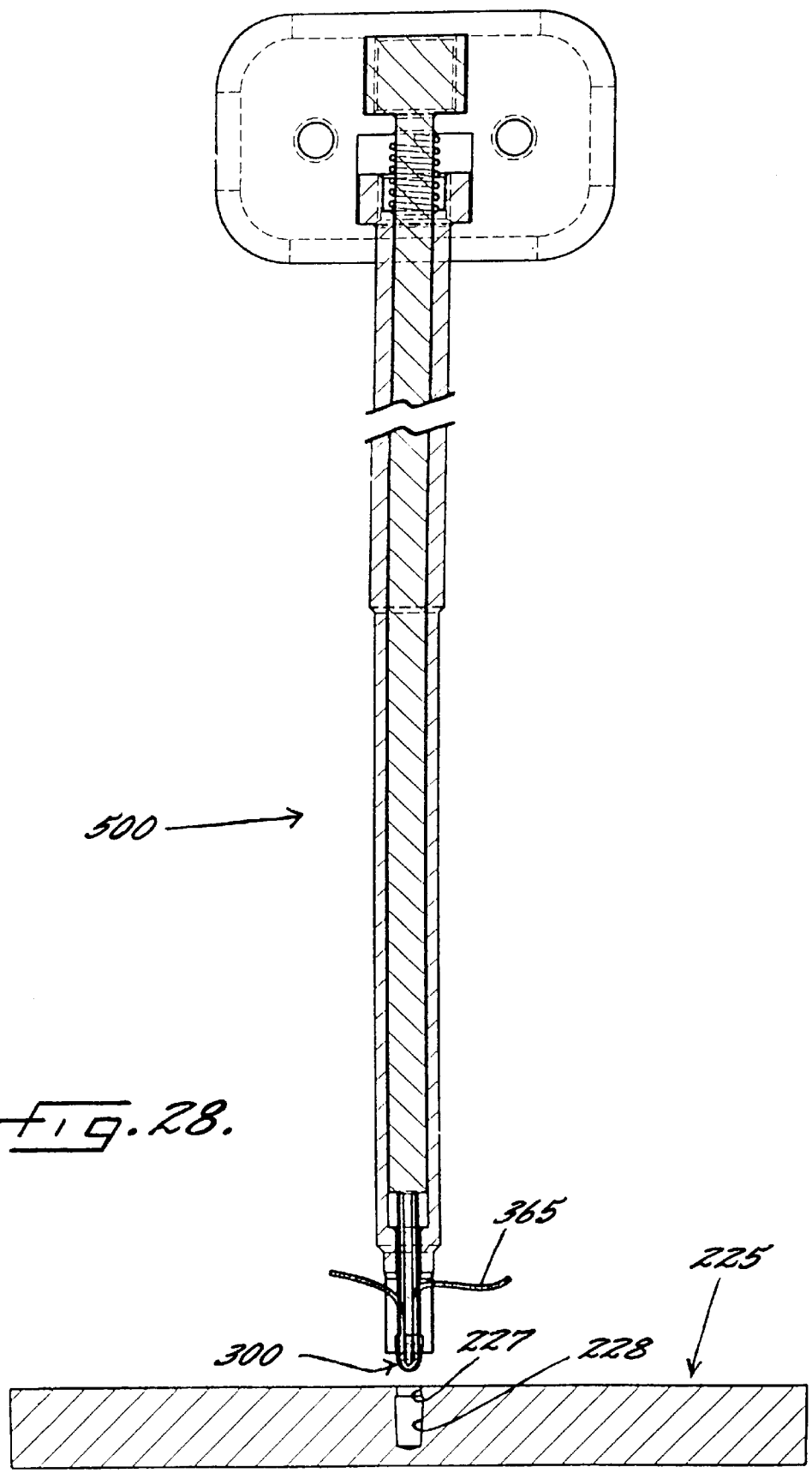
FIGS. 28–33 show the inserter device of FIG. 3 deploying the anchor of FIG. 2 in a workpiece.
Figure 29:
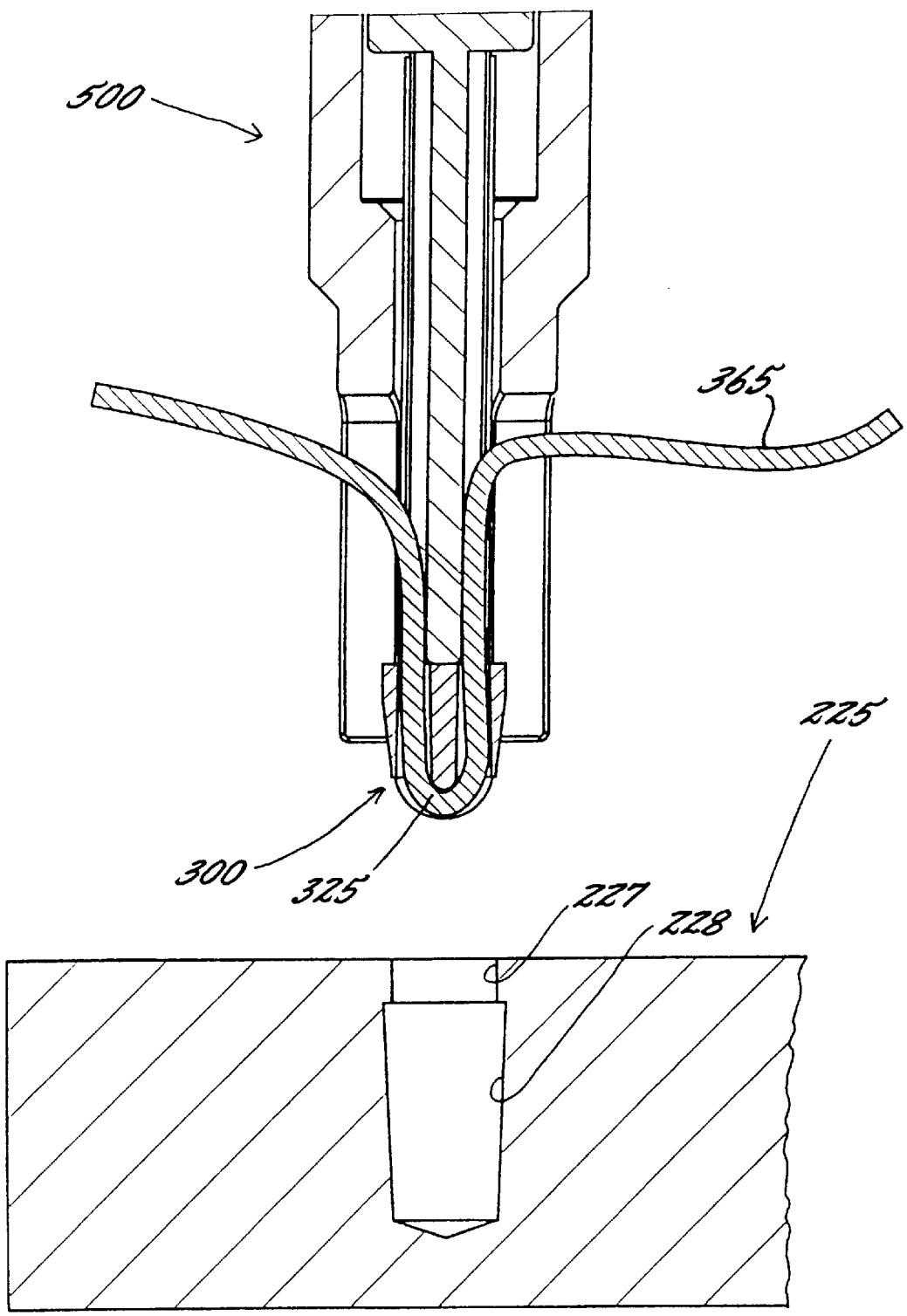
Figure 30:
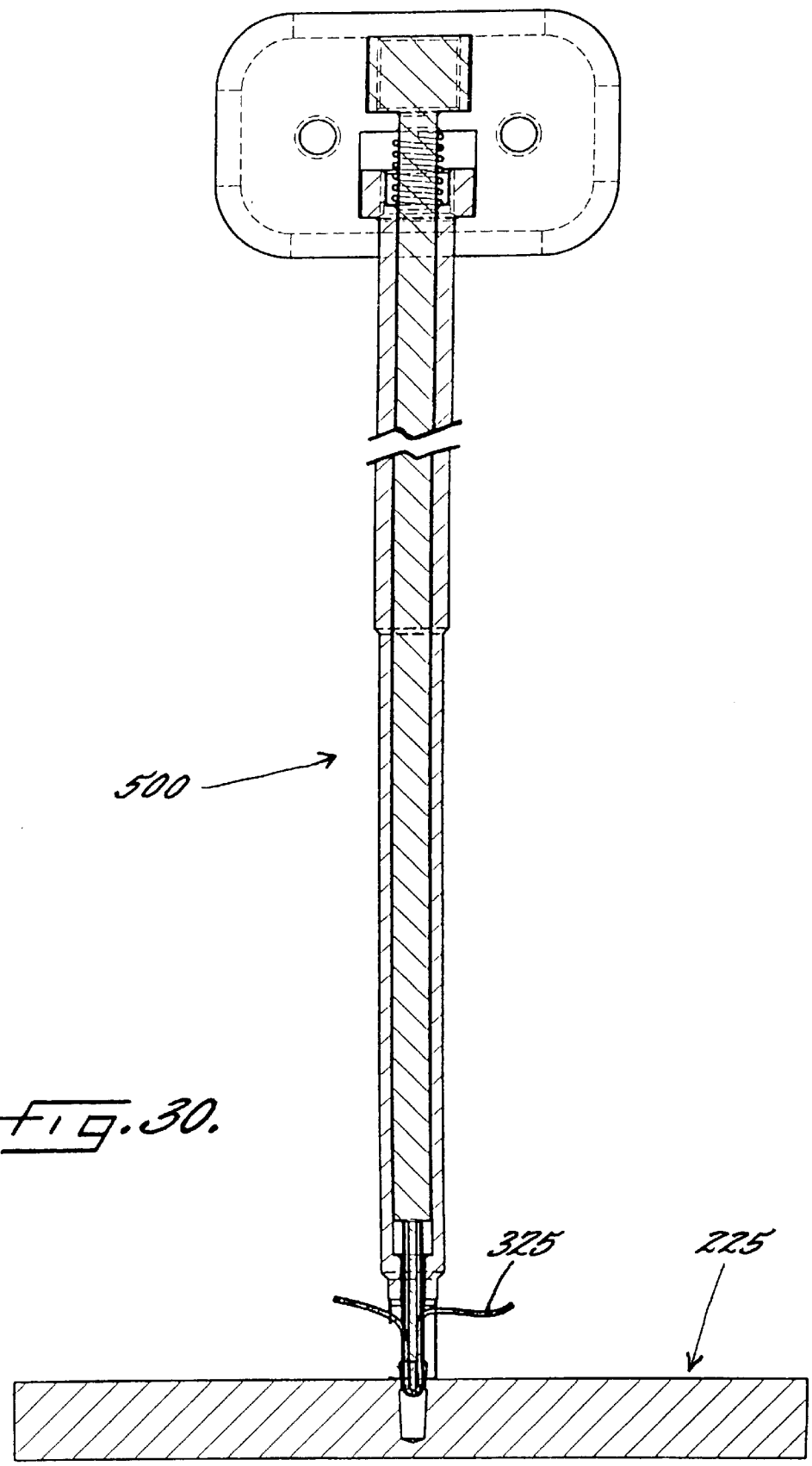
Figure 31:
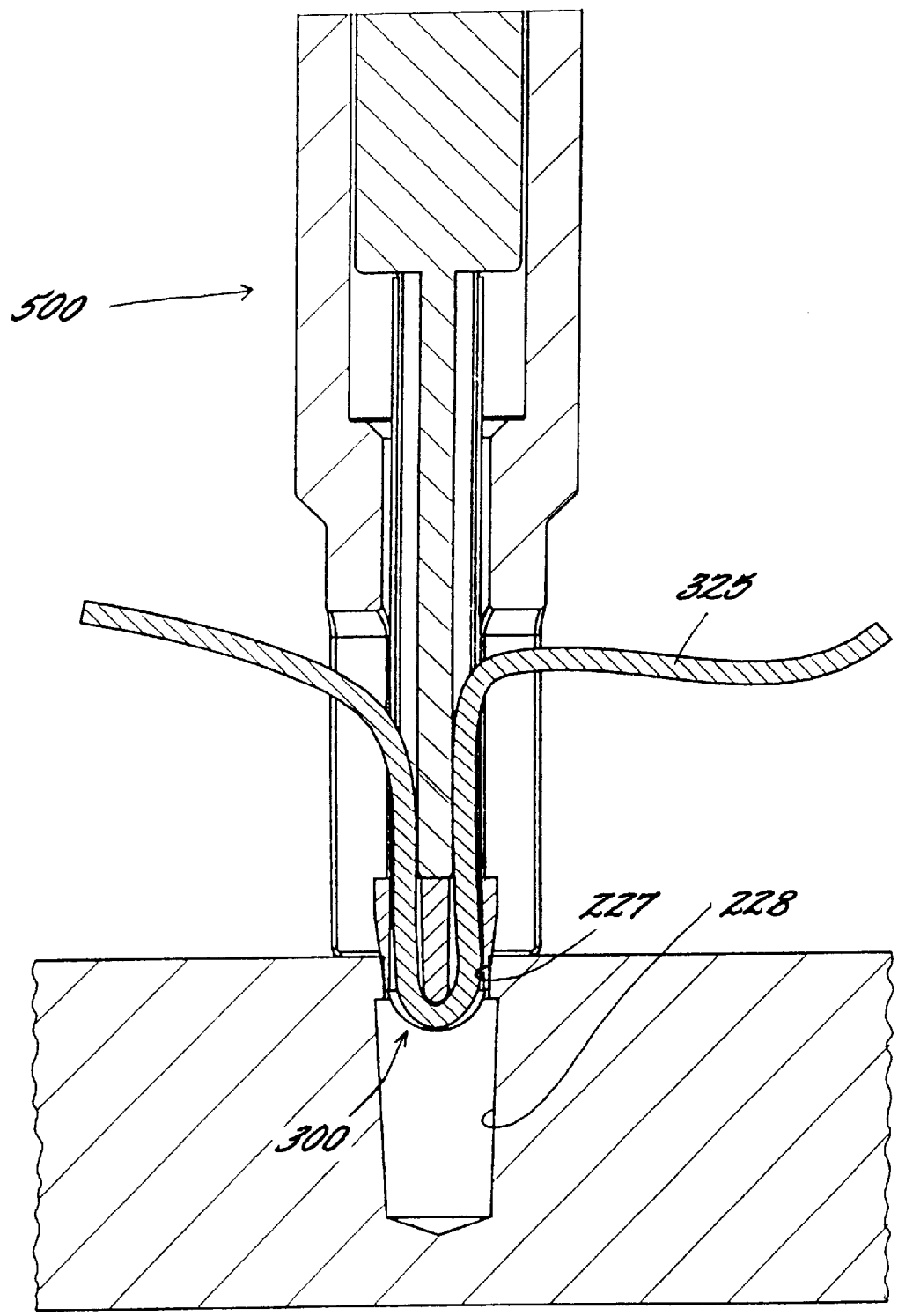

More specifically, as representatively shown in FIGS. 16–18, the handle 505 may conveniently be made in two identical halves 525. In its assembled form, handle 505 defines a drive rod mounting cavity 535, a sleeve/biasing means mounting cavity 540, and a sleeve/drive rod exit portal 545.

The drive rod 510, shown particularly in FIGS. 19–22, includes a shaft 550 having a distal end 555 and a proximal end 560, an enlarged proximal portion 565 attached to the proximal end 560, and an elongated tip portion 570 attached to the distal end 555. The enlarged proximal portion 565 is sized to fixedly engage the drive rod mounting cavity 535 in handle 505, with the shaft 550 extending outwardly therefrom through sleeve/biasing means mounting cavity 540 and exit portal 545. The elongated tip portion 570 has a smaller diametric cross-section than shaft 550, and shaft 550 and elongated tip portion 570 have a common longitudinal axis 575. Further, elongated tip portion 570 defines a pair of opposing longitudinal grooves 580 (FIG. 22) in its outer surface 585 which preferably extend along substantially the entire length of elongated tip portion 570. The grooves 580 are sized to receive the suture or other cord-like element 365 threaded through anchor body 305.

The biasing means 520, in the preferred embodiment of the invention, is a coil spring. The coil spring is located in sleeve/biasing means mounting cavity 540, co-axially surrounding shaft 550 of drive rod 510, and in engagement with the proximal shoulder 590 (FIG. 16) of cavity 540.

The sleeve 515, shown particularly in FIGS. 23–27, includes an elongated, hollow tubular member 595, a proximal end 600, a radially-extending flange 605 surrounding the tubular member at Its proximal end, a distal end 610, and a reduced diameter portion 615 adjacent to its distal end. The reduced diameter portion 615 defines a pair of opposing longitudinal slots 620 (FIG. 27) extending proximally from the distal end 610 for substantially the entire length of reduced diameter portion 615. The transverse width of slots 620 is such that the suture or other cord-like element 365 may be slidably received therein.

The sleeve 515 is disposed in telescoping relation over the drive rod shaft 550, with the sleeve's flange 605 located in the sleeve/biasing means mounting cavity 540, between the distal end of spring 520 and the forward end surface 621 (FIG. 16) of cavity 540, such that tubular member 595 is slidingly received in portal 545.

Thus it will be understood that handle 505 and drive rod 510 together form a substantially integral subassembly, with sleeve 515 adapted to reciprocate relative to the drive rod. In this regard it will be understood that the relative lengths of drive rod shaft 550 and tubular member 595 are selected such that, in their "normal" (i.e., with tubular member 595 in its outwardly-biased) position, the sleeve's reduced diameter portion 615 is disposed distally of the distal end of the tip portion 570 of the drive rod 510. This defines a cavity in the distal end of the inserter device 500 into which the anchor 300 may be placed and maintained by a frictional fit. At the same time, the sleeve's slots 620 permit a suture or other cord-like element 365 attached to the anchor to exit the sleeve.

Figure 32:
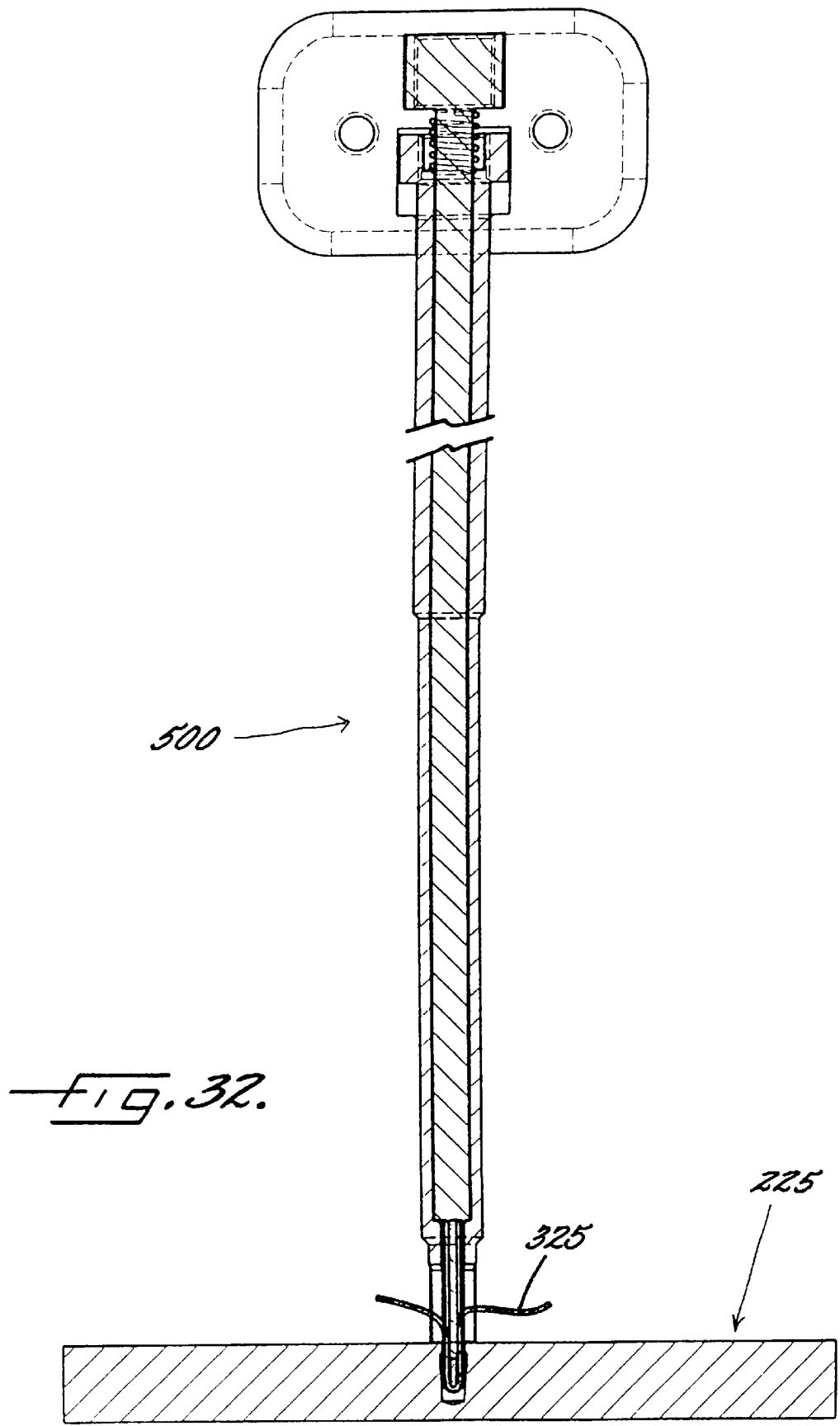
Figure 33:
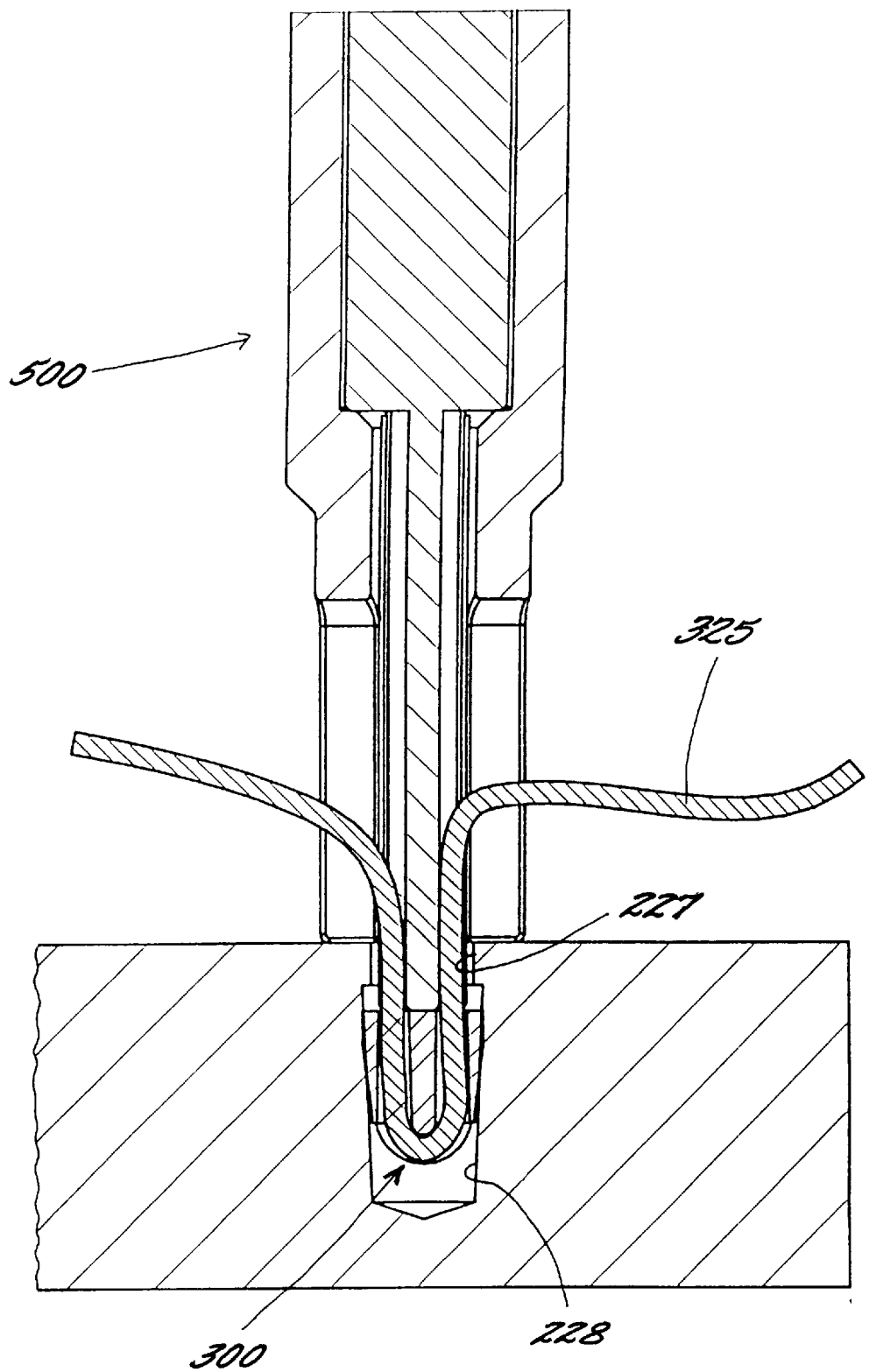

Accordingly, once the undercut hole in the workpiece has been formed by drill 100, the inserter device 500, with anchor 300 located within its distal end and with the suture or other cord-like element 365 threaded through the anchor and extending outwardly through the slots 620, may be used to insert the anchor into the undercut portion of the hole. More particularly, the distal end 610 of the sleeve may be brought into engagement with the surface 221 of the workpiece surrounding the upper bore 226 (FIGS. 28–31). Then, by pushing downwardly on the handle, the biasing force tending to hold the sleeve in its extended position may be overcome, thereby allowing the tip portion of the drive rod to engage the anchor and to drive it through upper bore 227 and down into the undercut portion 228 of the hole (FIGS. 32 and 33).

In so doing, the free ends of the suture or other cord-like element 365 enter the grooves 580 in drive rod 510 so as to avoid being crushed or broken during anchor deployment into the workpiece hole. At the same time, the resilient nature of anchor 300, in concert with the longitudinal bores 370, 375, 415 and 420 formed therein, allow the anchor to elastically collapse inwardly on itself far enough to pass through the smaller portion 227 of the hole and then re-expand to its normal share at the undercut portion 228 of the workpiece hole, thereby locking the anchor securely in the workpiece.

The foregoing concepts will be more fully understood by the following description of an example of the system and method of the present invention in a medical context.

Looking now to FIGS. 8–10 and 28–33, an example of the use of the invention to attach a length of suture 365 to a bone 225 is shown. In this context it should be understood that the nature of bone is such that the formation of an undercut hole is not always necessary. This is because some bones have natural internal cavities (e.g., the head of the tibia, the humeral head, etc.), and other types of bone have soft cancellous interiors distal to the outer cortical layer. In such a situation, an ordinary single-diameter bore may be formed in the bone. For the sake of the present description, however, it will be assumed that an undercut hole will be formed in the bone. With this understanding in mind, the method of the present invention may include the following steps.

First, an undercut hole is forked in the bone 225 using a drill 100 substantially as described above. Specifically, the distal cutting tip 205 of the drill head 110 is placed against the location on the surface 221 of bone 225 where it is desired to attach suture 365 (FIG. 8). The drill head 110 is then rotated about its longitudinal axis 195 while being urged axially toward the bone so as to cut into the bone (FIG. 9). This causes the drill head 110 to form a substantially cylindrical hole 227 in the bone.

Once the depth of the hole in the bone reaches a depth equal to the axial length of the drill head 110 plus the axial length of the connecting portion 160, the beveled corner 170 will engage the outer edge 226 of the hole. Thereafter, as the drill head is advanced further into the bone, its axis of rotation will be gradually shifted from longitudinal axis 195 to the longitudinal axis 120 by the tendency of the beveled corner 170 to center itself relative to the outer edge 226 of the hole. At the same time, the cutting flute 175 of re-centering element 125 will engage the outer edge 226 of the bone hole. The result of this is that the drill head 110 will gradually shift laterally so as to increase the diameter of the hole at a depth equal to the axial length of the connecting portion 160, while the cutting flute 175 countersinks the outer end of the hole. Thus, once the depth of the hole is equal to the axial length of the drill head 110 plus the connecting portion 160 plus the axial length of the beveled corner 170, the hole will have an outer portion 227 (FIG. 10) having a first diameter and an inner portion 228 having a second diameter larger than the first diameter.

The rotation of the drill 100 is then stopped and the shaft 105 is manipulated so as to align drill head 110 with the outer portion 227 of the hole. The drill head 110 may then be withdrawn from the hole.

A length of suture 365 is then threaded distally through bore 370 of anchor 300, across groove 335, and then proximally back through bore 375. The resulting anchor/suture assembly is then inserted, proximal end first, into the reduced diameter portion 615 of sleeve 515, with the free ends of suture 365 extending outwardly through slots 620. The anchor is held in this position by a friction fit. In this condition, the resulting inserter/anchor assembly is ready for use in deploying the anchor into the undercut portion of the bone hole.

If desired, the aforementioned inserter/anchor assembly may be pre-assembled at the time of manufacture and then packaged in a sterile package, with the sterile package being opened in the operating room at the tome of use.

Anchor 300 is deployed in the bone hole by bringing the distal end of sleeve 515 into engagement with the surface of the bone adjacent the hole (FIGS. 28–31). With the sleeve so positioned, a driving force is exerted distally on handle 505. Since the sleeve is fixed relative to the bone, this driving force causes the sleeve 515 to slide proximally in cavity 540, against the biasing spring 520, and forces the elongated tip portion 570 of drive rod 510 into the hole, pushing anchor 300 ahead of it (FIGS. 32 and 33).

As mentioned previously, the diameter of outer portion 227 of the bone hole is only slightly larger than the diameter of the intermediate portion 330 of anchor 300, and the proximal end 326 of anchor 300 has a generally rectangular shape large enough to contain an axial projection of intermediate portion 330. Hence, as the tapered distal portion 325, and intermediate portion 330, of anchor 300 enter the bone hole, they tend to align the anchor 300 with the hole. Thereafter, as drive rod 510 continues to force anchor 300 into the hole, the proximal portion of the anchor is distorted (i.e., compressed) inwardly so as to fit within the outer portion 227 of the hole. This is made possible by the resilience of the material used to form anchor 300, and by the presence of bores 370, 375, 415 and 420 adjacent to the four corners of the proximal portion of anchor 300.

More specifically, bores 415 and 420 are empty and extend through the proximal portion of anchor 300 into the intermediate portion thereof. This helps allow the proximal portion of anchor 300 to compress inwardly. Bores 370 and 375, on the other hand, are not empty, but rather contain suture 365. Nevertheless, since bores 370 and 375 are larger in diameter than suture 365, and since the suture is generally formed out of a woven material such that it may be radially compressed, bores 370 and 375 also help allow the proximal portion of the anchor to compress inwardly.

Once the proximal end of the anchor passes through the outer portion 227 of the hole, and into inner portion 228, the proximal portion of the anchor elastically returns to its original shape. Therefore, since the original shape of the anchor is too large to pass through the outer portion 227 of the bone hole, the anchor effectively and securely anchors the suture within the bone. Thereafter, inserter 500 may be removed, leaving the free ends of suture 365 extending out of the hole. This suture may hen be used to attach tissue (or some other object to the bone.

In the above regard, it is desirable that (a) the drive rod 510 exert force against as much of the proximal end of the anchor as possible, and (b) the suture not be crushed or damaged during the anchor insertion operation. The exertion of the driving force against as much of the proximal end of the anchor as possible helps keep the anchor from deviating from the longitudinal axis of the outer portion 227 of the hole during deployment. Hence, each of the corners of the large proximal end of the anchor well tend to deflect substantially equally inwardly, and the anchor will not tend to twist and bind in the outer portion 227 of the hole during insertion. To accomplish this, the elongated tip of the drive rod typically has a transverse cross-section of the same shape, but slightly smaller than, the transverse cross-section of the outer portion 227 of the hole. However, in order to protect the sutures, the elongated tip portion of the drive rod also has a pair of opposing grooves 580 in its outer surface. These grooves are sized to receive the free ends of the suture extending from the anchor while the elongated tip of the drive rod is located within the outer portion of the bone hole.

In the foregoing description of anchor 300, the proximal end 326 of the anchor is described as being substantially rectangular, with four corners 385, 390, 395 and 400, and with one of the bores 370, 375, 415 and 420 being positioned next to one of the corners 385, 390, 395 and 400. However, the proximal end 326 of anchor 300 could also be formed with some other polygonal shape, e.g., substantially triangular, in which case only three corners would be provided, and only one hole 415, 420 would be provided, in addition to the two suture holes 370, 375. Alternatively, the proximal end 326 of anchor 300 could be formed with a pentagonal shape, i.e., with five corners, in which case three holes 415, 420 would be provided, in addition to the two suture holes 370, 375; or the proximal end 326 of anchor 300 could be formed with a hexagonal shape, in which case four holes 415, 420 would be provided, in addition to the two suture holes 370, 375, etc. Preferably there are exactly as many holes 370, 375, 415 and 420 as there are corners to the proximal end 326 of anchor 300, with one hole aligned with each corner. In this way, appropriate space will be provided within the body of the anchor, into which the corners may radially deflect during insertion, so as to keep the body of the anchor from permanently deforming longitudinally during deployment.

It is also anticipated that the proximal end 326 of anchor 300 could be formed with a non-polygonal shape, e.g., circular or elliptical, in which case an appropriate number of holes 415, 420 are formed in the anchor in addition to the two suture holes 370, 375.

It should also be appreciated that cutting flute 175 might be omitted from drill 100 if desired.

Furthermore, it should be appreciated that, if desired, drill 100 might be removed from the bone hole while still rotating.

It should also be appreciated that the undercut hole might be formed in the bone or other workpiece using apparatus other than drill 100.

Also, the anchor 300 might be set in the bone or other workpiece using apparatus other than inserter device 500.

Having thus described an illustrative preferred embodiment of the system and method of the present invention, numerous modifications, variations, alterations and the like will occur to those skilled in the art. It is, therefore, intended that the foregoing specification be considered only as illustrative of the present invention, and that the invention be limited only by the terms of the appended claims.

What is claimed is:

1. A drill for forming an undercut hole in a workpiece, said drill comprising:

a shaft having a proximal end, a distal end and a first longitudinal axis;

a re-centering element attached to said distal end of said shaft, said re-centering element including a distally-tapering portion centered on a second longitudinal axis parallel to, but laterally spaced from, a projection of said first longitudinal axis;

a connecting member centered on said second longitudinal axis, said connecting member having a connecting member proximal end and a connecting member distal end, said connecting member extending distally from said re-centering member and being attached at said proximal end of said connecting member to said distally-tapering portion such that said connecting member and said distally-tapering portion together define a beveled corner centered on said second axis; and a substantially cylindrical drill head centered on an axial projection of said first longitudinal axis, said drill head having a proximal end, a distal cutting tip, an outer surface defining cutting flute means extending between said distal cutting tip and said drill head proximal end, and said drill head having a diameter larger than the diameter of said connecting member; and said proximal end of said drill head being eccentrically attached to said distal end of said connecting member.

2. A drill according to claim 1 wherein a handle is attached to said proximal end of said shaft.

3. A drill according to claim 1 wherein at least said distally-tapering portion of said re-centering element and said beveled corner together define at least one cutting flute adapted to countersink the undercut hole formed in said workpiece by said drill.

4. A system for attaching an object to a workpiece, said system comprising:

a drill for forming an undercut hole in a workpiece, said drill comprising:

a shaft having a proximal end, a distal end and a first longitudinal axis:

a re-centering element attached to said distal end of said shaft, said re-centering element including a distally-tapering portion centered on a second longitudinal axis parallel to, but laterally spaced from, a projection of said first longitudinal axis;

a connecting member centered on said second longitudinal axis, said connecting member having a connecting member proximal end and a connecting member distal end, said connecting member extending distally from said re-centering member and being attached at said proximal end of said connecting member to said distally-tapering portion such that said connecting member and said distally-tapering portion together define a beveled corner centered on said second axis; and a substantially cylindrical drill head centered on an axial projection of said first longitudinal axis, said drill head having a proximal end, a distal cutting tip, an outer surface defining cutting flute means extending between said distal cutting tip and said drill head proximal end, and said drill head having a diameter larger than the diameter of said connecting member;

said proximal end of said drill head being eccentrically attached to said distal end of said connecting member;

an anchor for securing a length of cord-like material in the undercut hole in the workpiece, said anchor comprising:

a body of resilient material including a longitudinal axis, a distal end, a distal portion adjacent to said distal end, a proximal end, a proximal portion adjacent to said proximal end, and an intermediate portion connecting said distal portion to said proximal portion;

said intermediate portion having a transverse cross-section sized to fit within the smallest transverse cross-section of said undercut hole in said workpiece;

said proximal end defining a substantially polygonal surface sized to contain an axial projection of said transverse cross-section of said intermediate portion;

said proximal portion tapering inwardly and distally from said proximal end so as to smoothly mate with said intermediate portion;

said distal portion curving inwardly and distally from said intermediate portion to said distal end, and said distal end defining a curved surface which smoothly mates with said distal portion;

said distal portion and said distal end together defining a substantially U-shaped groove extending from a first groove end adjacent said intermediate portion and located in alignment with one corner of said proximal end to a second groove end adjacent said intermediate portion and located in alignment with another corner of said proximal end;

said groove being sized to receive the length of the cord-like material therein;

a first bore extending from said first groove end to said proximal end of anchor, parallel to said longitudinal axis;

a second bore extending from said second groove end to said proximal end of said anchor, parallel to said longitudinal axis;

said first and second bores being sized to receive the length of the cord-like material therethrough; and a third bore extending into said proximal end of said anchor adjacent to another corner thereof, said third bore also being parallel to said longitudinal axis and extending through at least the proximal portion of said anchor; and an inserter for depolying a compressible anchor in the undercut hole in the workpiece, said inserter comprising:

a handle containing a biasing element;

a drive rod having a rod longitudinal axis, a rod distal end, a rod proximal end, and an axial length, said proximal end of said drive rod being attached to said handle; and a sleeve having a sleeve longitudinal axis, a sleeve proximal end, a sleeve distal end, and an axial length shorter than said axial length of said drive rod;

said sleeve being telescopically mounted co-axially over said drive rod and in engagement with said handle and said biasing element such that said sleeve is normally biased toward a first position wherein said sleeve distal end is located distally of said rod distal end so as to create an open cavity adapted to receive and frictionally retain at least a portion of the anchor, but may be moved proximally along said drive rod against said biasing element to a second position wherein said rod distal end projects axially and distally from said sleeve distal end.

5. A method for forming an undercut bore in a workpiece, said method comprising:
  (a) providing a drill having a predetermined axial length for forming an undercut hole in a workpiece, said drill comprising:
    a shaft having a proximal end, a distal end and a first longitudinal axis;
    a re-centering element attached to said distal end of said shaft, said re-centering element including a distally-tapering portion centered on a second longitudinal axis parallel to, but laterally spaced from, a projection of said first longitudinal axis;
    a connecting member having a predetermined axial length centered on said second longitudinal axis, said connecting member having a connecting member proximal end and a connecting member distal end, said connecting member extending distally from said re-centering member and being attached at said proximal end of said connecting member to said distally-tapering portion such that said connecting member and said distally-tapering portion together define a beveled corner centered on said second axis; and
    a substantially cylindrical drill head centered on an axial projection of said first longitudinal axis, said drill head having a proximal end, a distal cutting tip, an outer surface defining cutting flute means extending between said distal cutting tip and said drill head proximal end, and said drill head having a diameter larger than the diameter of said connecting member;
    said proximal end of said drill head being eccentrically attached to said distal end of said connecting member;
  (b) engaging said distal tip with the surface of said workpiece;
  (c) rotating said drill on said first longitudinal axis while urging said distal tip toward said workpiece so as to form a substantially cylindrical bore in said workpiece having a depth substantially equal to the axial length of said drill head plus the axial length of said connecting means;
  (d) further advancing said distal tip into said workpiece such that said beveled corner engages said bore, thereby shifting the axis of rotation of said drill head from said first longitudinal axis toward said second longitudinal axis and causing said drill head to enlarge the diameter of said bore below a depth substantially equal to the axial length of said connecting means; and
  (e) removing said drill head and said connecting means from said bore.

6. A method for attaching a length of cord-like material within an undercut hole in a workpiece, said method comprising the steps of:
  (a) providing:
    the length of cord-like material;
    a compressible anchor for securing the length of cord-like material in the undercut hole in the workpiece, said anchor comprising:
      a body of resilient material including a longitudinal axis, a distal end, a distal portion adjacent to said distal end, a proximal end, a proximal portion adjacent to said proximal end, and an intermediate portion connecting said distal portion to said proximal portion:
      said intermediate portion having a transverse cross-section sized to fit within the smallest transverse cross-section of said undercut hole in said workpiece;
      said proximal end defining a substantially polygonal surface sized to contain an axial projection of said transverse cross-section of said intermediate portion;
      said proximal portion tapering inwardly and distally from said proximal end so as to smoothly mate with said intermediate portion;
      said distal portion curving inwardly and distally from said intermediate portion to said distal end, and said distal end defining a curved surface which smoothly mates with said distal portion;
      said distal portion and said distal end together defining a substantially U-shaped groove extending from a first groove end adjacent said intermediate portion and located in alignment with one corner of said proximal end to a second groove end adjacent said intermediate portion and located in alignment with another corner of said proximal end;
      said groove being sized to receive the length of the cord-like material therein;
      a first bore extending from said first groove end to said proximal end of anchor, parallel to said longitudinal axis;
      a second bore extending from said second groove end to said proximal end of said anchor, parallel to said longitudinal axis;
      said first and second bores being sized to receive the length of the cord-like material therethrough; and
      a third bore extending into said proximal end of said anchor adjacent to another corner thereof, said third bore also being parallel to said longitudinal axis and extending through at least the proximal portion of said anchor; and
    an inserter for deploying the compressible anchor in the undercut hole in the workpiece, said inserter comprising:
      a handle containing a biasing element;
      a drive rod having a rod longitudinal axis, a rod distal end, a rod proximal end, and an axial length, said proximal end of said drive rod being attached to said handle; and
      a sleeve having a sleeve longitudinal axis, a sleeve proximal end, a sleeve distal end, and an axial length shorter than said axial length of said drive rod;
      said sleeve being telescopically mounted co-axially over said drive rod and in engagement with said handle and said biasing element such that said sleeve is normally biased toward a first position wherein said sleeve distal end is located distally of said rod distal end so as to create an open cavity adapted to receive and frictionally retain at least a portion of the anchor, but may be moved proximally along said drive rod against said biasing element to a second position wherein said rod distal end projects axially and distally from said sleeve distal end;

(b) threading said length of cord-like material distally through said first bore in said anchor, through said groove in said anchor, and proximally through said second bore in said anchor;

(c) with said inserter in said first position, inserting said anchor proximal end first into said cavity at said distal end of said sleeve and retaining the anchor in said cavity by a frictional fit;

(d) engaging said distal end of said sleeve with the surface of said workpiece immediately surrounding said undercut hole;

(e) exerting a driving force on said handle so as to move said sleeve from its first position relative to said drive rod to its second position relative to said drive rod and to advance said distal end of said drive rod into said opening pushing said anchor ahead of it, thereby elastically deforming said anchor; and (f) removing said drive rod from said opening and said distal end of said sleeve from said surface of said workpiece.

7. A method for attaching a length of cord-like material to a workpiece, said method comprising the steps of:

(a) providing:

the length of cord-like material;

a drill for forming an undercut hole in a workpiece, said drill comprising:

a shaft having a proximal end, a distal end and a first longitudinal axis;

a re-centering element attached to said distal end of said shaft, said re-centering element including a distally-tapering portion centered on a second longitudinal axis parallel to, but laterally spaced from, a projection of said first longitudinal axis;

a connecting member centered on said second longitudinal axis, said connecting member having a connecting member proximal end and a connecting member distal end, said connecting member extending distally from said re-centering member and being attached at said proximal end of said connecting member to said distally-tapering portion such that said connecting member and said distally-tapering portion together define a beveled corner centered on said second axis; and a substantially cylindrical drill head centered on an axial projection of said first longitudinal axis, said drill head having a proximal end, a distal cutting tip, an outer surface defining cutting flute means extending between said distal cutting tip and said drill head proximal end, and a said drill having a diameter larger than the diameter of said connecting member;

said proximal end of said drill head being eccentrically attached to said distal end of said connecting member;

an anchor for securing a length of cord-like material in the undercut hole in the workpiece, said anchor comprising:

a body of resilient material including a longitudinal axis, a distal end, a distal portion adjacent to said distal end, a proximal end, a proximal portion adjacent to said proximal end, and an intermediate portion connecting said distal portion to said proximal portion;

said intermediate portion having a transverse cross-section sized to fit within the smallest transverse cross-section of said undercut hole in said work-piece;

said proximal end defining a substantially polygonal surface sized to contain an axial projection of said transverse cross-section of said intermediate portion;

said proximal portion tapering inwardly and distally from said proximal end so as to smoothly mate with said intermediate portion;

said distal portion curving inwardly and distally from said intermediate portion to said distal end, and said distal end defining a curved surface which smoothly mates with said distal portion;

said distal portion and said distal end together defining a substantially U-shaped groove extending from a first groove end adjacent said intermediate portion and located in alignment with one corner of said proximal end to a second groove end adjacent said intermediate portion and located in alignment with another corner of said proximal end;

said groove being sized to receive the length of the cord-like material therein;

a first bore extending from said first groove end to said proximal end of anchor, parallel to said longitudinal axis;

a second bore extending from said second groove end to said proximal end of said anchor, parallel to said longitudinal axis;

said first and second bores being sized to receive the length of the cord-like material therethrough; and a third bore extending into said proximal end of said anchor adjacent to another corner thereof, said third bore also being parallel to said longitudinal axis and extending through at least the proximal portion of said anchor; and an inserter for deploying a compressible anchor in the undercut hole in the workpiece, said inserter comprising:

a handle containing a biasing element;

a drive rod having a rod longitudinal axis, a rod distal end, a rod proximal end, and an axial length, said proximal end of said drive rod being attached to said handle; and a sleeve having a sleeve longitudinal axis, a sleeve proximal end, a sleeve distal end, and an axial length shorter than said axial length of said drive rod;

said sleeve being telescopically mounted co-axially over said drive rod and in engagement with said handle and said biasing element such that said sleeve is normally biased toward a first position wherein said sleeve distal end is located distally of said rod distal end so as to create an open cavity adapted to receive and frictionally retain at least a portion of the anchor, but may be moved proximally along said drive rod against said biasing element to a second position wherein said rod distal end projects axially and distally from said sleeve distal end;

(b) forming the undercut hole in said workpiece with said drill by (1) engaging said distal tip of said drill head with the surface of said workpiece, (2) rotating said drill on said first axis while advancing said distal tip of said drill head into said workpiece to a depth equal to the axial length of said drill head plus the axial length of said connecting member, so as to form a substantially cylindrical bore in said workpiece, (3) advancing said distal tip further into said workpiece so as to force said beveled corner into said hole thereby causing the axis of rotation of said drill head to shift from said first longitudinal axis toward said second longitudinal axis and said drill head to radially enlarge the inner portion of said hole, and (4) removing said drill head and said connecting member from said bore through the outer, unenlarged portion of thereof, (c) threading said length of cord-like material distally through said first bore in said anchor, through said groove in said anchor, and proximally through said second bore in said anchor;

(d) with said inserter in said first position, inserting said anchor proximal end first into said cavity at said distal end of said sleeve and retaining the anchor in said cavity by a frictional fit;

(e) engaging said distal end of said sleeve with the surface of said workpiece immediately surrounding said undercut hole;

(f) exerting a driving force on said handle so as to move said sleeve from its first position relative to said drive rod to its second position relative to said drive rod and to advance said distal end of said drive rod into said undercut hole pushing said anchor ahead of it, thereby elastically deforming said anchor as it passes through said non-enlarged portion of said undercut hole and allowing said anchor to expand to its original shape upon the completion of its entry into the enlarged portion of said undercut hole; and (g) removing said drive rod from said undercut hole and said distal end of said sleeve from said surface of said workpiece.

* * * * *